(12) United States Patent
O'Bryant et al.

(10) Patent No.: US 11,525,834 B2
(45) Date of Patent: Dec. 13, 2022

(54) BLOOD-BASED SCREEN FOR DETECTING NEUROLOGICAL DISEASES IN PRIMARY CARE SETTINGS

(71) Applicants: University of North Texas Health Science Center at Fort Worth, Fort Worth, TX (US); Board of Regents, The University of Texas System, Austin, TX (US)

(72) Inventors: Sid E. O'Bryant, Aledo, TX (US); Robert C. Barber, Benbrook, TX (US); Guanghua Xiao, Coppell, TX (US); Dwight German, Dallas, TX (US)

(73) Assignees: University of North Texas Health Science Center at Fort Worth, Forth Worth, TX (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/904,244

(22) PCT Filed: Jul. 9, 2014

(86) PCT No.: PCT/US2014/046015
§ 371 (c)(1),
(2) Date: Jan. 11, 2016

(87) PCT Pub. No.: WO2015/006489
PCT Pub. Date: Jan. 15, 2015

(65) Prior Publication Data
US 2016/0154010 A1    Jun. 2, 2016

Related U.S. Application Data

(60) Provisional application No. 61/845,121, filed on Jul. 11, 2013.

(51) Int. Cl.
*G01N 33/68* (2006.01)
*G16B 25/00* (2019.01)
*G16B 20/20* (2019.01)
*G16B 25/10* (2019.01)
*A61B 5/00* (2006.01)
*G16B 20/00* (2019.01)
*G16B 20/40* (2019.01)

(52) U.S. Cl.
CPC ....... *G01N 33/6896* (2013.01); *A61B 5/4088* (2013.01); *G16B 20/00* (2019.02); *G16B 20/20* (2019.02); *G16B 20/40* (2019.02); *G16B 25/00* (2019.02); *G16B 25/10* (2019.02); *G01N 2570/00* (2013.01); *G01N 2800/28* (2013.01); *G01N 2800/2814* (2013.01); *G01N 2800/2821* (2013.01); *G01N 2800/2835* (2013.01); *G01N 2800/387* (2013.01)

(58) Field of Classification Search
CPC .......... G01N 33/6896; G01N 2800/28; G01N 2800/387; A61B 5/4088
See application file for complete search history.

(56) References Cited

U.S. PATENT DOCUMENTS

| 5,192,753 | A | 3/1993 | McGeer et al. |
| 5,819,956 | A | 10/1998 | Rinderer |
| 7,598,049 | B2 * | 10/2009 | Ray .................. G01N 33/6896 435/7.21 |
| 3,008,025 | A1 | 8/2011 | Zhang |
| 8,430,816 | B2 | 4/2013 | Avinash et al. |
| 2006/0094064 | A1 | 5/2006 | Sandip et al. |
| 2009/0075395 | A1 | 3/2009 | Lee et al. |
| 2010/0233818 | A1 | 9/2010 | Sekiyama |
| 2010/0280562 | A1 | 11/2010 | Pi et al. |
| 2011/0082187 | A1 | 4/2011 | Campbell et al. |
| 2011/0159527 | A1 | 6/2011 | Schlossmacher et al. |
| 2012/0238835 | A1 | 9/2012 | Hyde et al. |
| 2012/0238837 | A1 | 9/2012 | Hyde et al. |
| 2012/0295281 | A1 | 11/2012 | Rai et al. |

(Continued)

FOREIGN PATENT DOCUMENTS

| WO | 9840061 A1 | 9/1998 |
| WO | 2006020269 A2 | 2/2006 |

(Continued)

OTHER PUBLICATIONS

Laske, et al., "Immune Profiling in Blood Identifies sTNF-R1 Performing Comparably Well as Biomarker Panels for Classification of Alzheimer's Disease Patients." Journal of Alzheimer's Disease, Jan. 2013, vol. 34, No. 2, pp. 367-375.

Braskie, M.N., et al., "Neuroimaging measures as endophenotypes in Alzheimer's disease," International Journal of Alzheimer's Disease, Feb. 7, 2011, 16 pp.

Cruchaga, C., "Cerebrospinal fluid APOE levels: an endophenotype for genetic studies for Alzheimer's disease," Human Molecular Genetics. Jul. 13, 2012, pp. 1-14.

(Continued)

*Primary Examiner* — Olga N Chernyshev
(74) *Attorney, Agent, or Firm* — Saul Ewing Arnstein & Lehr LLP; Kathryn Doyle; Domingos J. Silva

(57) ABSTRACT

The present invention includes methods and kits for the diagnosing a neurological disease within primary care settings comprising: obtaining a blood test sample from a subject, measuring IL-7 and TNFα biomarkers in the blood sample, comparing the level of the one or a combination of biomarkers and neurocognitive screening tests with the level of a corresponding one or combination of biomarkers in a normal blood sample and neurocognitive screening tests, and predicting that an increase in the level of the blood test sample in relation to that of the normal blood sample indicates that the subject is likely to have a neurological disease.

6 Claims, 7 Drawing Sheets

(56) References Cited

U.S. PATENT DOCUMENTS

| | | |
|---|---|---|
| 2013/0012403 A1 | 1/2013 | Hu |
| 2014/0018446 A1 | 1/2014 | Royall et al. |
| 2014/0147863 A1 | 5/2014 | O'Bryant et al. |
| 2014/0220568 A1 | 8/2014 | Inze et al. |
| 2014/0315736 A1 | 10/2014 | Nagele |
| 2015/0241454 A1 | 8/2015 | Sandip et al. |
| 2016/0291036 A1 | 10/2016 | O'Bryant |
| 2017/0356903 A1 | 12/2017 | Domenyuk et al. |
| 2019/0219599 A1 | 7/2019 | O'Bryant et al. |
| 2019/0234967 A1 | 8/2019 | O'Bryant |

FOREIGN PATENT DOCUMENTS

| | | |
|---|---|---|
| WO | 2007094472 A1 | 8/2007 |
| WO | 2007144194 A1 | 12/2007 |
| WO | 20100118035 A2 | 10/2010 |
| WO | WO2011143597 A1 | 11/2011 |
| WO | 2014066318 A1 | 5/2014 |
| WO | 2015006489 A1 | 1/2015 |
| WO | 2015006489 A8 | 1/2015 |
| WO | 2015081166 A1 | 6/2015 |
| WO | 2017223291 A1 | 12/2017 |
| WO | 2019143562 A1 | 7/2019 |

OTHER PUBLICATIONS

During, E.H., et al., "The concept of FDG-PET endophenotype in Alzheimer's disease," Neurol Sci., Aug. 2011, vol. 32, pp. 559-569.

Edwards, M., et al., "Combining Select Neuropsychological Assessment with Blood-Based Biomarkers to Detect Mild Alzheimer's Disease: A Molecular Neuropsychology Approach," Journal of Alzheimer's Disease, vol. 42, Apr. 2014, pp. 635-640.

Gottesman, I.I., et al., "The endophenotype concept in psychiatry: etymology and strategic intentions," American Journal of Psychiatry, Apr. 2003; 160(4), pp. 636-645.

Hall, J. R., et al., "Biomarkers of Vacular Risk, Systemic Inflammation, and Microvascular Pathology and Neuropsychiatric Symptoms in Alzheimer's Disease," Journal of Alzheimer's Disease, vol. 35, Jan. 2013, pp. 363-371.

International Search Report and Written Opinion of KIPO for PCT/US2014/067562 dated Mar. 6, 2015, 12 pp.

Janocko, N.J., et al., "Neuropathologically defined subtypes of Alzheimer's disease differ significantly from neurofibrillary tangle-predominant dementia," Acta Neuropathologica, Nov. 2012, vol. 124(5), pp. 681-692.

Johnson, L.A., et al., "A Depressive Endophenotype of Mild Cognitive Impairment and Alzheimer's Disease," PLoS ONE, Jul. 11, 2013, vol. 8:7, e68848, 8 pp.

Johnson, L. A., et al., "Comorbid Depression and Diabetes as a Risk for Mild Cognitive Impairment and Alzheimer's Disease in Elderly Mexican Americans," Journal of Alzheimer's Disease, vol. 47, Apr. 2015, pp. 129-136.

Nilufer, E-T, "Gene expression endophenotypes: a novel approach for gene discovery in Alzheimer's disease," Molecular Neurodegeneration, 2011, vol. 6:31, 18 pp.

O'Bryant, S.E., et al., "Decreased C-Reactive Protein Levels in Alzheimer Disease," J. Geriatr. Psychiatry Neurol., Mar. 2010, vol. 23(1), pp. 49-53.

O'Bryant, S.E., et al., "A Serum Protein-Based Algorithm for the Detection of Alzheimer Disease," Arch. Neurol., Sep. 2010, vol. 67(9), pp. 1077-1081.

O'Bryant, S.E., et al., "Serum Brain-Derived Neurotrophic Factor Levels are Specifically Associated with Memory Performance among Alzheimer's Disease Cases," Dement Geriatr Cogn Disord., Dec. 7, 2010, vol. 31, pp. 31-36.

O'Bryant, S.E., et al., "Characterization of Mexican Americans with Mild Cognitive Impairment and Alzheimer's Disease," Journal of Alzheimer's Disease, vol. 33, Aug. 2012, pp. 373-379.

O'Bryant, S.E., et al., "Comparing biological markers of Alzheimer's Disease Across Blood Fraction and Platforms: Comparing Apples to Oranges," Alzheimer's & Dementia: Diagnosis, Assessment & Disease Monitoring, vol. 3, 2016, pp. 27-34.

O'Bryant, S.E., et al., "Guidelines for the Standardization of Preanalytic Variables for Blood-Based Biomarker Studies in Alzheimer's Disease Research," Alzheimer's & Dementia, 2014, pp. 1-12.

O'Bryant, S.E., et al., "Molecular Neurospychology: Creation of Test-Specific Blood Biomarker Algorithms," Dement. Geriatr. Cogn. Disord., Oct. 2013, vol. 37, pp. 45-47.

O'Bryant S.E., et al., "Validation of a serum screen for Alzheimer's disease across assay platforms, species and tissues," Journal of Alzheimer's Disease, vol. 42, No. 4, Jan. 1, 2014, pp. 1325-1335.

Swardfager, et al., "A meta-analysis of cytokines in Alzheimer's disease," Biological Psychiatry, vol. 68, No. 10, 2010, pp. 930-941.

Alzheimer's Association: "Alzheimer's Disease Facts and Figures", Alzheimer's & Dementia vol. 9, Issue 2, Mar. 2013, pp. 208-245.

Belmin J., et al., "Assessment and Management of Patients with Cognitive Impairment and Dementia in Primary Care." The Journal of Nutrition, Health & Aging, vol. 16, Nov. 5, 2012, pp. 462-467.

Benadiba M., et al., "New Molecular Targets for PET and SPECT Imaging in Neurodegenerative Diseases," Rev. Bras. Psiquiatr., Oct. 2012;34 (Suppl2):S125-S148.

Bjerke M., et al., "Confounding Factors Influencing Amyloid Beta Concentration in Cerebrospinal Fluid," International Journal of Alzheimer's Disease, vol. 2010, Jun. 7, 2010, pp. 1-11.

Breiman L., "Random Forests" Learning Machines, Oct. 2001, vol. 45, Issue 1, pp. 5-32.

Dickstein DL., et al., "Role of Vascular Risk Factors and Vascular Dysfunction in Alzheimer's Disease," Mt. Sinai. J. Med., 77(1), Aug. 2010, pp. 82-102.

Duff K., et al., "Utility of the RBANS in Detecting Cognitive Impairment Associated with Alzheimer's Disease Sensitivity, Specificity, and Positive and Negative Predictive Powers," Archives of Clinical Neuropsychology 23 (2008) pp. 603-612.

Duff K., et al., "Diagnostic Accuracy of the RBANS in Mild Cognitive Impairment: Limitations on Assessing Milder Impairments," Archives of Clinical Neuropsychology, vol. 25, Jun. 21, 2010, pp. 429-441.

International Search Report and Written Opinion of KIPO for PCT/US2014/046015 dated Oct. 22, 2014, 15 pp.

Kounnas MZ., et al., "Modulation of g-Secretase Reduces b-Amyloid Deposition in a Transgenic Mouse Model of Alzheimer's Disease," Neuron 67, Sep. 9, 2010, pp. 769-780.

Laske C., et al., "Identification of a Blood-based Biomarker Panel for Classification of Alzheimer's Disease," International Journal of Neuropsychopharmacology, Feb. 12, 2011, pp. 1147-1155.

Lopponen M., et al., "Diagnosing cognitive impairment and dementia in primary health care—a more active approach is needed," Age and Ageing vol. 32:6, Apr. 2003, pp. 606-612.

Martin MA, et al., "Recruitment of Mexican-American Adults for an Intensive Diabetes Intervention Trial," Ethnicity and Disease, 21(1), 2011, pp. 7-12.

McKhann G., et al., "Clinical diagnosis of Alzheimer's disease: Report of the NINCDS-ADRDA Work Group* under the auspices of Department of Health and Human Services Task Force on Alzheimer's Disease," Neurology, vol. 34, Jul. 1984, pp. 939-944.

O'Bryant S.E., et al., "Discrepancies between self-reported years of education and estimated reading level among elderly community-dwelling African-Americans: Analysis of the MOAANS data," Archives of Clinical Neuropsychology, vol. 22, 2007, pp. 327-332.

O'Bryant S.E., et al., "Brain-Derived Neurotrophic Factor Levels in Alzheimer's Disease," J. Alzheimers Dis., Jun. 2009, vol. 17(2), pp. 337-341.

O'Bryant S.E., et al., "A Serum Protein-Based Algorithm for the Detection of Alzheimer's Disease," Arch Neurol., Sep. 13, 2010, vol. 67(9), pp. 1077-1081.

O'Bryant S.E., et al., "A Blood-Based Screening Tool for Alzheimer's Disease that Spans Serum and Plasma: Findings from TARC and ADNI," Findings from TARC and ADNI, PLoS One, Dec. 2011, vol. 6(12), pp. 1-8.

O'Bryant S.E., et al., "A Blood-Based Algorithm for the Detection of Alzheimer's Disease," Dementia and Geriatric Cognitive Disorders, Aug. 24, 2011, vol. 32, pp. 55-62.

(56) References Cited

OTHER PUBLICATIONS

O'Bryant S.E., et al., "Biomarkers of Alzheimer's Disease Among Mexican Americans," J. Alzheimers Dis., Dec. 2007, pp. 1-9.
O'Bryant S.E., et al., "Manuscript in Press: Dementia & Geriatric Cognitive Disorders: Molecular Neuropsychology: Creation of Test-Specific Blood Biomarker Algorithms," Dement. Geriatr. Cogn. Disord., Apr. 17, 2015, 37(0), pp. 45-57.
Oh E.S., et al., "Comparison of Conventional ELISA with Electrochemiluminescence Technology for Detection of Amyloid-B in Plasma," J. Alzheimers Dis., 2010, vol. 21(3), pp. 769-773.
Okereke O.I., et al., "A profile of impaired insulin degradation in relation to late-life cognitive decline: A preliminary investigation," Int. J. Geriatr. Phsychiatry, Feb. 2009, vol. 24(2), pp. 177-182.
Reddy M.M., et al., "Identification of Candidate IgG Biomarkers for Alzheimer's Disease via Combinatorial Library Screening," Cell (144), Jan. 7, 2011, pp. 132-142.
Thal L.J., et al., "The Role of Biomarkers in Clinical Trials for Alzheimer Disease," Alzheimer Dis. Assoc. Disord., 2006, vol. 20(1), pp. 6-15.
Doecke, J.D., et al., "Blood-Based Protein Biomarkers for Diagnosis of Alzheimer Disease," Arch. Neurol., vol. 69(10), Jul. 16, 2012, pp. 1318-1325.
Extended European Search Report for 14822061.9 dated Nov. 23, 2016, 12 pp.
O'Bryant S.E., et al., "Biomarkers of Alzheimer's Disease Among Mexican Americans," J. Alzheimers Dis., vol. 34(4), Dec. 2012, pp. 841-849.
Yokono, Koichi, "Alzheimer Disease as a diabetic complication," Japanese Journal of Geriatrics, 2010, vol. 47, pp. 385-389.
Barber, R., et al. (Guanghua Xiao), "An Inflammatory Endophenotype of Alzheimer's Disease," Poster Presentation, Alzheimer's and Dementia 2010, 6(f) Supplement: S530, 1 pg.
Extended European Search Report for 14865107.8 dated Jul. 24, 2017, 12 pp.
Humpel, Christian, "Identifying and validating biomarkers for Alzheimer's disease," Trends in Biotechnology, Jan. 2011, vol. 29, No. 1, pp. 26-32.
International Search Report and Written Opinion of KIPO for PCT/US2017/038712 dated Sep. 20, 2017, 16 pp.
Thaker, G., "Schizophrenia Endophenotypes as Treatment Targets," Expert Opin Ther Targets (2007), 11(9):1189-1206.
Australian Government, IP Australia, 1st Examination Report for Australian Patent Appl. No. 2017268567 dated Feb. 15, 2019, 4 pp.
Chan, E., et al., "Expression Analyses and molecular biological studies contribute to a systems-level understanding of host response, and new analytical software tools can help," Drug Discovery & Development, Apr. 1, 2006, pp. 1-4.
Colangelo, V., et al., "Gene Expression Profiling of 12633 Genes in Alzheimer Hippocampal CA1: Transcription and Neurotrophic Factor Down-Regulation and Up-Regulation of Apoptotic and Pro-Inflammatory Signaling," Journal of Neuroscience Research, May 10, 2002, vol. 70, pp. 462-473.
Coleman, R., "Of mouse and man—what is the value of the mouse in predicting gene expression in humans?" DDT, vol. 8, No. 6, Mar. 2003, 3 pp.
Whitehead, A., et al., "Variation in tissue-specific gene expression among natural populations," Genome Biology, Jan. 26, 2005, vol. 6, pp. R13.1 to R13.14.
American Gerontological Society "The Gerontological Society of American Workgroup on Cognitive Impairment Detection: Report and Recommendations". 2015.
Anonymous "Clinical and neuropathological criteria for frontotemporal dementia" The Lund and Manchester Groups. Journal of Neurology, Neurosurgery, and Psychiatry. 1994;57(4 (Print)):416-418.
Arora, et al. "Diagnostic accuracy of point-of-care testing for diabetic ketoacidosis at emergency-department triage: 3-hydroxybutyrate versus the urine dipstick" Diabetes Care. Apr. 2011;34(4):852-854.
Bandason, et al. "Validation of a screening tool to identify older children living with HIV in primary care facilities in high HIV prevalence settings" AIDS 2016;30(5):779-785.

Bhavadharini, et al. "Use of capillary blood glucose for screening for gestational diabetes mellitus in resource-constrained settings" Acta Diabetologica 2016,53(1):91-97.
Biomarkers Definitions Working Group "Biomarkers and surrogate endpoints: preferred definitions and conceptual framework" Clin Pharmacol Ther.69:89-95. Mar. 2001.
Birrer, et al. "Depression in later life: A diagnostic and therapeutic challenge" American Family Physician. May 2004;69(10):2375-2382.
Campari, et al. "Impact of the Introduction of Digital Mammography in an Organized Screening Program on the Recall and Detection Rate" Journal of Digital Imaging. 2016;29(2):235-242.
Connell, et al. "Black and white adult family members' attitudes toward a dementia diagnosis" Journal of the American Geriatrics Society. Sep. 2009;57(9):1562-1568.
Cummings, et al. "Fit-for-purpose biomarker method validation for application in clinical trials of anticancer drugs" British Journal of Cancer, published online Oct. 5, 2010;103(9):1313-1317.
Emre, et al. "Clinical Diagnostic Driteria for Dementia Associated with Parkinson's Disease" Movement Disorders. 2007;22(12):1689-1707.
Fillit, et al. "Economics of dementia and pharmacoeconomics of dementia therapy" American Journal Geriatric Pharmacotherapy. Mar. 2005;3(1):39-49.
Harvey, et al. "A systematic review of the diagnostic accuracy of prostate specific antigen" BMC Urology. Sep. 10, 2009; 9(1).
Hurd, et al. "Monetary Costs of Dementia in the United States" New England Journal of Medicine. Apr. 4, 2013;368(14):1326-1334.
Knopman, et al. "Patterns of Care in the Early Stages of Alzheimer's Disease: Impediments to Timely Diagnosis" Journal of the American Geriatrics Society. 2000;48(3):300-304.
Lee, et al. Fit-for-Purpose Method Development and Validation for Successful Biomarker Measurement. Pharmaceutical Research. Feb. 2006; 23(2):312-328.
Lee, et al. "The National Mammography Database: Preliminary Data" American Journal of Roentgenology. Apr. 2016; 206(4):883-890.
Lundquist, et al. Screening for Alzheimer's Disease: Inspiration and Ideas from Breast Cancer Strategies. Journal of Applied Gerontology. 2015;34(3):317-328.
Mueller, et al. "Ways toward an early diagnosis in Alzheimer's disease: The Alzheimer's Disease Neuroimaging Initiative (ADNI)" Alzheimer's and Dementia. 2005;1(1):55-66.
Novak KR, J. "Hispanics/Latinos and Alzheimer's Disease" Alzheimer's Association; May 18, 2004.
O'Bryant, et al. "Estimating the Predictive Value of the Test of Memory Malingering: An Illustrative Example for Clinicians" Clinical Neuropsychologist. 2006;20(3):533-540.
Petersen, Ronald C. "Mild Cognitive Impairment Clinical Trials" Nature, Aug. 2003, vol. 2, pp. 646-653.
Petersen, et al. "Mild Cognitive Impairment: An Overview" CNS Spectrums. Jan. 2008; 13(1):45-53.
Piper, et al. "Diagnostic and Predictive Accuracy of Blood Pressure Screening Methods with Consideration of Rescreening Intervals: A Systematic Review for the U.S. Preventive Services Task Force" Annals of Internal Medicine. Feb. 2015;162(3):192-204.
Plumb, et al. "Sensitivity and specificity of CT colonography for the detection of colonic neoplasia after positive faecal occult blood testing: Systematic review and meta-analysis" European Radiology, published online Feb. 12, 2014;24(5):1049-1058.
Canadian Intellectual Property Office, Examination Report for Canadian Appl. No. 2,920,474 dated Apr. 3, 2017, 4 pp.
Canadian Intellectual Property Office, Examination Report for Canadian Appl. No. 2,920,474 dated Dec. 28, 2017, 4 pp.
Canadian Intellectual Property Office, Examination Report for Canadian Appl. No. 2,920,474 dated Oct. 15,2018, 5 pp.
European Patent Office, Communication pursuant to Article 94(3) EPC for EP Application No. 14822061.9 dated Jan. 7, 2019, 5 pp.
European Patent Office, Communication pursuant to Article 94(3) EPC for EP Application No. 14822061.9 dated Mar. 29, 2018, 7 pp.
Canadian Intellectual Property Office, Examination Report for Canadian Appl. No. 2,920,474 dated Jun. 28, 2019, 8 pp.

(56) References Cited

OTHER PUBLICATIONS

Japan Patent Office, Notification of Reasons for Refusal for Japanese Patent Appl. No. 20117-198118 dated Aug. 22, 2019, with translation. 8 pp.
Villarreal, et al. "Serum-based protein profiles of Alzheimer's disease and mild cognitive impairment in elderly Hispanics" Neurodegener Dis Manag. 2016,6(3), 203-213.
Kim, et al. "Interactions between pro-inflammatory cytokines and statins on depression in patients with acute coronary syndrome" Prog Neuropsychopharmacol Biol Psychiatry, 2018. 80(Pt C): p. 250-254.
Kosaka, et al. "Presenile dementia with Alzheimer-, Pick- and Lewy-body changes" Acta neuropathologica, 1976. 36(3): p. 221-33.
Kuhle, et al. "A highly sensitive electrochemiluminescence immunoassay for the neurofilament heavy chain protein" Journal of Neuroimmunology. 2010;220(1-2):114-119.
Landers, et al. "A High-Intensity Exercise Boot Camp for Persons With Parkinson Disease: A Phase II, Pragmatic, Randomized Clinical Trial of Feasibility, Safety, Signal of Efficacy, and Disease Mechanisms" J Neurol Phys Ther, 2019. 43(1): p. 12-25.
Liu, et al. "Specifically neuropathic Gaucher's mutations accelerate cognitive decline in Parkinson's" Ann Neurol, 2016. 80(5): p. 674-685.
Liu, et al. "Prediction of cognition in Parkinson's disease with a clinical-genetic score: a longitudinal analysis of nine cohorts" Lancet Neurol, 2017. 16(8): p. 620-629.
Lo, et al. "Relationship between patient age and duration of physician visit in ambulatory setting: Does one size fit all?" Journal of the American Geriatrics Society. 2005;53(7):1162-1167.
Locascio, et al. "Association between alpha-synuclein blood transcripts and early, neuroimaging-supported Parkinson's disease" Brain, 2015. 138(Pt 9): p. 2659-71.
Maeck, et al. Dementia diagnostics in primary care: a representative 8-year follow-up study in lower saxony, Germany. Dementia & Geriatric Cognitive Disorders. 2008;25(2):127-134.
McKeith, et al. An evaluation of the predictive validity and inter-rater reliability of clinical diagnostic criteria for senile dementia of Lewy body type. Neurology. 1994;44(5):872-877.
McKeith, et al. Diagnosis and management of dementia with Lewy bodies: Fourth consensus report of the DLB Consortium. Neurology, 2017. 89(1): p. 88-100.
McKeith, et al. Operational criteria for senile dementia of Lewy body type (SDLT). Psychological medicine, 1992. 22(4): p. 911-22.
McKeith, et al. Sensitivity and specificity of dopamine transporter imaging with 123I-FP-CIT SPECT in dementia with Lewy bodies: a phase III, multicentre study. Lancet Neurology, 2007. 6(4): p. 305-313.
Mckeith, et al. The clinical diagnosis and misdiagnosis of senile dementia of Lewy body type (SDLT). British Journal of Psychiatry. 1994;165(SEP.):324-332.
Mollenhauer, et al. "Serum heart-type fatty acid-binding protein and cerebrospinal fluid tau: marker candidates for dementia with Lewy bodies" Neurodegener Dis, 2007. 4(5): p. 366-75.
Murray, et al. "MRI and pathology of REM sleep behavior disorder in dementia with Lewy bodies" Neurology, 2013. 81(19): p. 1681-9.
Nakamura, et al. High performance plasma amyloid-beta biomarkers for Alzheimer's disease. Nature, 2018. 554(7691): p. 249-254.
Park, et al. "Differential Diagnosis of Patients with Inconclusive Parkinsonian Features Using [18F]FP-CIT PET/CT" Nuclear Medicine and Molecular Imaging, 2014.(Published Online Dec. 11, 2013) 48(2): p. 106-113.
Piazza, et al. "Increased tissue factor pathway inhibitor and homocysteine in Alzheimer's disease" Neurobiology of Aging. 2010.
Postuma, et al. "MDS clinical diagnostic criteria for Parkinson's disease" Mov Disord, 2015. 30(12): p. 1591-601.
Pykkö, et al. "APOE4 predicts amyloid- in cortical brain biopsy but not idiopathic normal pressure hydrocephalus" Journal of Neurology, Neurosurgery and Psychiatry. 2012;83(11):1119-1124.

R Development Core Team "R: A language and environment for statistical computing" 2009; www.R-project.org. Version 3.6.0 Apr. 26, 2019.
Scherzer, et al. Molecular markers of early Parkinson's disease based on gene expression in blood. Proc Natl Acad Sci U S A 2007. 104: p. 955-960.
Scherzer, et al. GATA transcription factors directly regulate the Parkinson's disease-linked gene alpha-synuclein. Proc Natl Acad Sci U S A, Aug. 5, 2008. 105(31): p. 10907-12.
Schneider, et al. "Biological marker candidates of alzheimer's disease in blood, plasma, and serum". CNS Neuroscience and Therapeutics. 2009;15(4):358-374.
Shaw, et al. "Biomarkers of neurodegeneration for diagnosis and monitoring therapeutics" Nature Reviews. Drug Discovery. Apr. 2007;6(4):295-303.
Shtilbans, et al. "Biomarkers in Parkinson's disease: An update" Current Opinion in Neurology, 2012. 25(4): p. 160-465.
Sinha, et al. Biomarkers in dementia with Lewy bodies: A review. International Journal of Geriatric Psychiatry, 2012. 27(5): p. 443-453.
Sudduth, et al. "Neuroinflammatory phenotype in early Alzheimer's disease." Neurobiology of Aging, Apr. 2013, vol. 34, pp. 1051-1059.
Sverzellati, et al. "Low-dose computed tomography for lung cancer screening: comparison of performance between annual and biennial screen" European Radiology. 2016:1-9.
Szerlip, et al. "Association of cognitive impairment with chronic kidney disease in Mexican Americans" Journal of the American Geriatric Society. 2015;63(10):2023-2028.
Van Blitterswijk, et al. "Anti-superoxide dismutase antibodies are associated with survival in patients with sporadic amyotrophic lateral sclerosis" Amyotroph Lateral Scler, 2011. 12(6): p. 430-8.
Van Oijen, et al. "Plasma Abeta(1-40) and Abeta(1-42) and the risk of dementia: a prospective case-cohort study" [see comment]. Lancet Neurology 2006;5(8):655-660.
Van Den Dungen, et al. "The accuracy of family physicians' dementia diagnoses at different stages of dementia: A systematic review" International Journal of Geriatric Psychiatry. 2012;27(4):342-354.
Villemagne, et al. "Long night's journey into the day: Amyloid-β imaging in Alzheimer's disease" Journal of Alzheimer's Disease. 2013;33(Suppl. 1):S349-S359.
Waring, et al. for the Texas Alzheimer's Research Consortium. "The Texas Alzheimer's Research Consortium longitudinal research cohort: Study design and baseline characteristics" Texas Public Health Journal. 2008;60(3):9-13.
Watson, et al. Screening accuracy for late-life depression in primary care: A systematic review. Journal of Family Practice. Dec. 2003;52(12):956-964.
Wildburger, et al. Amyloid-beta Plaques in Clinical Alzheimer's Disease Brain Incorporate Stable Isotope Tracer in Vivo and Exhibit Nanoscale Heterogeneity. Front Neurol, Mar. 22, 2018. 9: p. 169.
Wright, et al. Geographic and ethnic variation in Parkinson disease: a population-based study of US Medicare beneficiaries. Neuroepidemiology, (published online Jan. 15, 2010) 2010. 34(3): p. 143-51.
Akiyama, et al. "Inflammation and Alzheimer's disease" Neurobiol Aging. May-Jun. 2000;21(3):383-421.
Al-Jarrah, et al. Treadmill exercise training could attenuate the upregulation of Interleukin-1 beta and tumor necrosis factor alpha in the skeletal muscle of mouse model of chronic/progressive Parkinson disease. NeuroRehabilitation, 2018.
Alves, et al. "CSF amyloid-p and tau proteins, and cognitive performance, in early and untreated Parkinson's Disease: The Norwegian ParkWest study" Journal of Neurology, Neurosurgery and Psychiatry. 2010;81(10):1080-1086.
Anonymous "Consensus report of the Working Group on: Molecular and Biochemical Markers of Alzheimer's Disease". The Ronald and Nancy Reagan Research Institute of the Alzheimer's Association and the National Institute on Aging Working Group.[see comment][erratum appears in Neurobiol Aging May-Jun. 1998;19(3):285] Neurobiology of Aging. 1998;19(2):109-116.
Australian Government, IP Australia, 1st Examination Report for Australian Patent Appl. No. 2014354808 dated Feb. 14, 2017, 5 pp.

(56) References Cited

OTHER PUBLICATIONS

Australian Government, IP Australia, 2nd Examination Report for Australian Patent Appl. No. 2014354808 dated Apr. 11, 2017, 4 pp.
Australian Government, IP Australia, 1st Examination Report for Australian Patent Appl. No. 2018201062 dated Jul. 22, 2019, 5 pp.
Barker, et al. Relative frequencies of Alzheimer disease, Lewy body, vascular and frontotemporal dementia, and hippocampal sclerosis in the State of Florida Brain Bank. Alzheimer Dis Assoc Disord, 2002. 16(4): p. 203-12.
Bauer, et al. "Examining the test of memory malingering trial 1 and word memory test immediate recognition as screening tools for insufficient effort" Assessment. 2007;14(3):215-222.
Blasko, I. "Ibuprofen diecreases cytokine-indduced amyloid beta production in neuronal cells" Neurobiology of Disease, Dec. 2001, (6) 1094-1101.
Bond, et al. "Screening for cognitive impairment, Alzheimer's disease and other dementias: Opinions of European caregivers, payors, physicians and the general public" Journal of Nutrition, Health and Aging. 2010;14(7):558-562.
Britschgi, et al. "Blood protein signature for the early diagnosis of Alzheimer's disease" Archives of Neurology, 66(2); 161-165, Feb. 2009.
Brothers, et al. "Are inflammatory profiles the key to personalized Alzheimer's treatment?" Neurodegenerative Disease Management, Aug. 2013, vol. 3, pp. 343-351.
Chatterjee, et al. Comparative analysis of RNA-Seq data from brain and blood samples of Parkinson's disease. Biochem Biophys Res Commun, 2017.
Cho, et al. Selective translational control of the Alzheimer amyloid precursor protein transcript by iron regulatory protein-1. J Biol Chem, 2010. 285(41): p. 31217-32.
Clark, et al. "Diagnostic accuracy of% retention scores on RBANS verbal memory subtests for the diagnosis of Alzheimer's disease and mild cognitive impairment" Archives of Clinical Neuropsychology 2010;25(4):318-326.
Clarke, et al. "Advances in blood-based protein biomarkers for Alzheimer's disease" Alzheimer's Research and Therapy, 5(3); 18, May 9, 2013.
Colloby, et al. "A comparison of 99mTc-exametazime and 123I-FP-CIT SPECT imaging in the differential diagnosis of Alzheimer's disease and dementia with Lewy bodies" International Psychogeriatrics, 2008. 20(6): p. 1124-1140.
Ding, et al. Association of SNCA with Parkinson: replication in the Harvard NeuroDiscovery Center Biomarker Study. Mov Disord, 2011. 26(12): p. 2283-6.
Edwards, et al. Molecular markers of amnestic mild cognitive impairment among Mexican Americans. J Alzheimers Dis, 2016. 49(1): p. 221-8.
Eller, et al. α-Synuclein in Parkinson disease and other neurodegenerative disorders. Clinical Chemistry and Laboratory Medicine, 2011. 49(3): p. 403-408.
Elsafi, et al. "The sensitivity, specificity, predictive values, and likelihood ratios of fecal occult blood test for the detection of colorectal cancer in hospital settings" Clinical and Experimental Gastroenterology. Sep. 9, 2015;8:279-284.
European Patent Office, Communication pursuant to Article 94(3) EPC for EP Application No. 148651078.8 dated Jun. 14, 2018, 5 pp.
Fan, et al., "Structural and functional biomarkers of prodromal Alzheimer's disease: a high-dimensional pattern classification study," Neuroimage, vol. 41, No. 2, 2008, pp. 227-285.
Ferman, et al. Inclusion of RBD improves the diagnostic classification of dementia with Lewy bodies. Neurology., 2011. 77(9): p. 875-882.
Ferreti, et al. "Intracellular Aβ-oligomers and early inflammation in a model of Alzheimer's disease" Neurobiology of Aging, vol. 33, Issue 7, Jul. 2012, pp. 1329-1342.
Fiss, et al. Cognitive impairment in primary ambulatory health care: Pharmacotherapy and the use of potentially inappropriate medicine. International Journal of Geriatric Psychiatry. 2013;28(2):173-181.
Fujishiro, et al. Validation of the neuropathologic criteria of the third consortium for dementia with lewy bodies for prospectively diagnosed cases. Journal of Neuropathology and Experimental Neurology, Jul. 2008. 67(7): p. 649-656.
Gerlach, et al. "Biomarker candidates of neurodegeneration in Parkinson's disease for the evaluation of disease-modifying therapeutics" Journal of Neural Transmission, 2012. 119(1): p. 39-52.
Gold, et al. The emergence of diagnostic imaging technologies in breast cancer: Discovery, regulatory approval, reimbursement, and adoption in clinical guidelines. Cancer Imaging, 2012. 12(1): p. 13-24.
Gotttesman, et al., Genetic theorizing and schizophrenia. British Journal of Psychiatry. 1973;122(566):15-30.
Graff-Radford, et al. Imaging and acetylcholinesterase inhibitor response in dementia with Lewy bodies. Brain, 2012. 135(8): p. 2470-2477.
Green, et al. "Alterations of p11 in brain tissue and peripheral blood leukocytes in Parkinson's disease" Proc Natl Acad Sci U S A, 2017.
Groveman, et al. Rapid and ultra-sensitive quantitation of disease-associated alpha-synuclein seeds in brain and cerebrospinal fluid by alphaSyn RT-QuIC. Acta Neuropathol Commun, 2018. 6(1): p. 7.
Hakimi, et al. Parkinson's disease-linked LRRK2 is expressed in circulating and tissue immune cells and upregulated following recognition of microbial structures. J Neural Transm, 2011. 118(5): p. 795-808.
Halliday, et al. Neuropathology underlying clinical variability in patients with synucleinopathies. Acta neuropathologica, 2011. 122(2): p. 187-204.
Hampel, et al. "Precision Medicine: The Golden Gate for detection, treatment and prevention of Alzheimer's disease" Journal of Prevention of Alzheimer's Disease, Dec. 2016. 3(4): p. 243-259.
Hansson, et al. Blood-based NfL: A biomarker for differential diagnosis of parkinsonian disorder. Neurology, Mar. 7, 2017. 930-937.
Hely, et al. The Sydney multicenter study of Parkinson's disease: the inevitability of dementia at 20 years. Mov Disord, Apr. 2008. 23(6): p. 837-44.
Henchcliffe, et al. Biomarkers of Parkinson's disease and Dementia with Lewy bodies. Progress in Neurobiology, 2011. 95(4): p. 601-613.
Hennecke, et al. RNA biomarkers of Parkinson's disease: developing tools for novel therapies. Biomark Med, 2008, 2(1): p. 41-53.
Henriksen, et al. "The future of blood-based biomarkers for Alzheimer's disease" Alzheimer's & Dementia, in press, 2013 (Published online Jul. 11, 2013).
Higuchi, et al. "Glucose hypometabolism and neuropathological correlates in brains of dementia with Lewy bodies" Experimental Neurology, 2000. 162(2): p. 247-256.
Ho, et al. "Bridging molecular genetics and biomarkers in Lewy body and related disorders" International Journal of Alzheimer's Disease, 2011.
Hu, et al. Biomarker discovery for Alzheimer's disease, frontotemporal lobar degeneration, and Parkinson's disease. Acta Neuropathologica, 2010 (Published Online Jul. 22, 2010) 120(3): p. 385-399.
Hu, et al. "Transcriptional modulator H2A histone family, member Y (H2AFY) marks Huntington disease activity in man and mouse" Proc Natl Acad Sci USA, 2011. 108(41): p. 17141-6.
Huse, et al. "Burden of illness in Parkinson's disease" Mov Disord, 2005. 20(11): p. 1449-54.
Jani, et al. "Recommendations for Use and Fit-for-Purpose Validation of Biomarker Multiplex Ligand Binding Assays in Drug Development" AAPS Journal, vol. 18, No. 1, Jan. 2016.
Kaerst, et al. "Using cerebrospinal fluid marker profiles in clinical diagnosis of dementia with lewy bodies, Parkinson's disease, and Alzheimer's disease" Journal of Alzheimer's Disease, 2014. 38(1): p. 63-73.
Kantarci, et al. Multimodality Imaging Characteristics of Dementia with Lewy bodies. Neurobiology of aging, 2012. 33(9): p. 2091-105.
EP Communication and Partial European Search Report dated Nov. 12, 2020, for corresponding European Patent Application 20 187 559.8.

(56) References Cited

OTHER PUBLICATIONS

International Search Report and Written Opinion for PCT/US2020/018297 dated Jun. 23, 2020.
Adapt Research Group, et al., "Naproxen and celecoxib do not prevent AD in early results from a randomized controlled trial", Neurology, vol. 68, 2007, pp. 1800-1808.
Aisen, et al., "Effects of Rofecoxib or Naproxen vs Placebo on Alzheimer disease progression: a randomized controlled trial", JAMA, vol. 289, No. 21, Jun. 4, 2003, pp. 2819-2826.
Aisen, et al., "Neither Rofecoxib Nor Naproxen Slows Cognitive Decline in People With Mild-To-Moderate Alzheimer's Disease", Evidence-Based Healthcare, vol. 7, 2003, pp. 200-201.
Anthony, et al., "Reduced prevalence of AD in users of NSAIDs and H2 receptor antagonists: the Cache County study", Neurology, vol. 54, 2000, pp. 2066-2071.
Breitner, et al., "Extended resits of the Alzheimer disease anti-inflammatory prevention trial (ADAPT)", Alzheimers Dement, vol. 7, No. 4, Jul. 2011, pp. 402-411.
Cunningham, et al., "Oxidative stress, testosterone, and cognition among Caucasian and Mexican American men with and without Alzheimer's disease", J Alzheimers Dis, vol. 40, No. 3, 2014, pp. 563-573.
Duong, et al., "C-reactive Protein-Like Immunoreactivity in the Neurofibrillary Tangles of Alzheimer's Disease", Brain Res, vol. 749, 1997, pp. 152-156.
Durrenberger, et al., "Common mechanisms in neurodegeneration and neuroinflammation: a BrainNet Europe gene expression microarray study", J Neural Trans, vol. 122, 2015, pp. 1055-1068.
Edwards, et al., "Molecular markers of neuropsychological functioning and Alzheimer's disease", Alzheimer's & Dementia: Diagnosis, Assessment & Disease Monitoring, vol. 1, No. 1, Mar. 1, 2015, pp. 61-66.
Etminan, et al., "Effect of non-steroidal anti-inflammatory drugs on risk of Alzheimer's disease: systematic review and meta-analysis of observational studies", BMJ, vol. 327, Jul. 19, 2003, pp. 128-132.
Gasparini, et al., "Non-steroidal anti-inflammatory drugs (NSAIDs) in Alzheimer's disease: old and new mechanisms of action", J Neurochem, vol. 91, 2004, pp. 521-536.
Gotschall, P. E., "β-amyloid induction of gelatinase B secretion in cultured microglia: inhibition by dexamethasone and indomethacin", NeuroReport, vol. 7, No. 18, 1996, pp. 3077-3080.
Grundman, et al., "Treatment of Alzheimer's Disease: Rationale and Strategies", Neurologic Clinics, vol. 18, 2000, pp. 807-827.
Hall, et al., "The impact of APOE status on relationship of biomarkers of vascular risk and systemic inflammation to neuropsychiatric symptoms in Alzheimer's disease", J Alzheimer's Dis, vol. 40, 2014, pp. 887-896.
Heneka, et al., "Innate immune activation in neurodegenerative disease", Nat Rev Immunol, vol. 14, 2014, pp. 463-477.
Hirohata, et al., "Non-steroidal anti-inflammatory drugs have anti-amyloidogenic effects for Alzheimer's β-amyloid fibrils in vitro", Neuropharmacol, vol. 49, 2005, pp. 1088-1099.
In't Veld, B.A., et al., "Nonsteroidal Antiinflammatory Drugs and the Risk of Alzheier's Diesease", N Engl J Med, vol. 345, No. 21, 2001, pp. 1515-1521.
Iwamoto, et al., "Demonstration of GRP immunoreactivity in brains of Alzheimer's disease: immunohistochemical study using formic acid pretreatment of tissue sections", Neurosci Lett, vol. 177, 1994, pp. 23-26.

Johnson, et al., "A depressive endophenotype of poorer cognition among cognitively healthy community—dwelling adults: Results from the Western Australia Memory Study", Intl J Geriatr Psychiatry, vol. 30, No. 8, 2015, pp. 881-886.
Klegeris, et al., "Non-steroidal anti-inflammatory drugs (NSAIDs) and other anti- inflammatory agents in the treatment of neurodegenerative disease", Curr Alzheimer Res, vol. 2, 2005, pp. 355-365.
Koyama, et al., "The Role of Peripheral Inflammatory Markers in Dementia and Alzheimer's Disease: A Meta-Analysis", J Geronol A Biol Sci Med Sci, vol. 68, No. 4, Apr. 2013, pp. 433-440.
Leung, et al., "Inflammatory Proteins in Plasma are Associated with Severity of Alzheimer's Disease", PLoS One, vol. 8, Issue 6, Jun. 2013, pp. e64971 (1-10).
Lyketsos, et al., "Developing new treatments for Alzheimer's disease: The who, what, when, and how of biomarker-guided therapies", Int Psychogeriatr, vol. 20, No. 5, 2008, pp. 871-889.
Mackenzie, et al., "Nonsteroidal anti-inflammatory drugs use and Alzheimer-type pathology in aging", Neurology, vol. 50, 1998, pp. 986-990.
McGeer, et al., "The importance of inflammatory mechanisms in Alzheimer disease", Exp Gerontol, vol. 33, No. 5, 1998, pp. 371-378.
Netland, et al., "Indomethacin reverses the microglial response to amyloid βprotein", Neurobiol Aging, vol. 19, No. 3, 1998, pp. 201-204.
D'Bryant, et al., "A blood screening test for Alzheimer's disease", Alzheimer's & Dementia: Diagnosis, Assessment & Disease Monitoring, vol. 3, Jun. 25, 2016, pp. 83-90.
D'Bryant, et al., "A Proinflammatory Endophenotype Predicts Treatment Response in a Multicenter Trial of NSAIDS in AD", Alzheimer's & Dementia: The Journal of the Alzheimer's Association, vol. 10, No. 4, supplement, 2014, p. 273-p. 274.
O'Bryant, et al., "Risk factors for mild cognitive impairment among Mexican Americans", Alzheimers Dement, vol. 9, No. 6, 2013, pp. 622-631.
O'Bryant, et al., "Texas Research and Care Consortium. The Link between C-reactive protein and Alzheimer's disease among Meixcan Americans", J Alzheimers Dis, vol. 34, No. 7, Jan. 1, 2013, pp. 701-706.
Pasinetti, et al., "Clycooxygenase-2 expression is increased in frontal cortex of Alzheimer's disease brain", Neuroscience, vol. 87, No. 2, 1998, pp. 319-324.
Richartz, et al., "Decline of Immune Responsiveness: A Pathogenetic Factor in Alzheimer's Disease?", J Psychiatric Res, vol. 39, 2005, pp. 535-543.
Rogers, et al., "Clinical trial of indomethacin in Alzheimer's disease", Neurology, vol. 43, 1993, pp. 1609-1611.
Schmidt, et al., "Early inflammation and dementia: a 25-year follow-up of the Honolulu-Asia Aging Study", Ann Neurol, vol. 52, 2002, pp. 168-174.
Thal, et al., "A Randomized, Double-Blind, Study of Rofecoxib in Patients with Mild Cognitive Impairment", Neuropsychopharmacology, vol. 30, 2005, pp. 1204-1215.
Thal, et al., "The Role of Biomarkers in Clinical Trials for Alzheimer Disease", Alzheimer Dis Assoc Disord, 20(1), 2006, pp. 6-15.
Tocco, et al., "Maturational regulation and regional induction of cyclooxygenase-2 in rat brain: implications for Alzheimer's disease", Exp Neurol, vol. 144, Article No. EN976429, 1997, pp. 339-349.

* cited by examiner

| | Screen Result | | Specialist Referral |
|---|---|---|---|
| Serum Screen in Primary Care Setting | Alzheimer's Disease | → | Memory Disorders Specialist |
| | Parkinson's Disease | → | Movement Disorders Specialist |
| | Dementia with Lewy Bodies | → | Specialty Clinic for DLB patients |
| | Frontotemporal Dementia | → | Specialty Clinic for FTD patients and inclusion of psychiatry |
| | Down's syndrome | → | Neurodevelopmental disease specialist and genetic testing/counseling |

*FIG. 7*

BLOOD-BASED SCREEN FOR DETECTING NEUROLOGICAL DISEASES IN PRIMARY CARE SETTINGS

CROSS REFERENCE TO RELATED APPLICATIONS

This application claims priority to, and is the National Phase of International Application No. PCT/2014/046015, filed Jul. 9, 2014, which claims priority under 35 U.S.C. § 119(e) from U.S. Provisional Application No. 61/845,121 filed Jul. 11, 2013, all of which are hereby incorporated by reference in their entireties.

STATEMENT OF FEDERALLY FUNDED RESEARCH

This invention was made with U.S. Government support by the National Institutes of Health under Grant Numbers AG039389 and AG012300. The government has certain rights in this invention.

FIELD OF INVENTION

The present invention relates in general to the field of screening, detecting and discriminating between neurological diseases within primary care settings, and more particularly, to biomarkers for the detection, screening, and discriminating patients with neurological diseases.

BACKGROUND ART

Without limiting the scope of the invention, its background is described in connection with neurological diseases.

The detection and evaluation of disease conditions has progressed greatly as a result of the sequencing of the human genome and the availability of bioinformatics tools. One such system is taught in U.S. Pat. No. 8,430,816, issued to Avinash, et al., for a system and method for analysis of multiple diseases and severities. Briefly, these inventors teach a data processing technique that includes a computer-implemented method for accessing reference deviation maps for a plurality of disease types. The reference deviation maps may include subsets of maps associated with severity levels of respective disease types and a disease severity score may be associated with each severity level. The method is said to also include selecting patient severity levels for multiple disease types based on the subsets of reference deviation maps. Also, the method may include automatically calculating a combined patient disease severity score based at least in part on the disease severity scores associated with the selected patient severity levels, and may include outputting a report based at least in part on the combined patient disease severity score.

Another such invention, is taught in U.S. Pat. No. 8,008,025, issued to Zhang and directed to biomarkers for neurodegenerative disorders. Briefly, this inventor teaches methods for diagnosing neurodegenerative disease, such as Alzheimer's Disease, Parkinson's Disease, and dementia with Lewy body disease by detecting a pattern of gene product expression in a cerebrospinal fluid sample and comparing the pattern of gene product expression from the sample to a library of gene product expression pattern known to be indicative of the presence or absence of a neurodegenerative disease. The methods are also said to provide for monitoring neurodegenerative disease progression and assessing the effects of therapeutic treatment. Also provided are kits, systems and devices for practicing the subject methods.

United States Patent Application Publication No. 2013/0012403, filed by Hu is directed to Compositions and Methods for Identifying Autism Spectrum Disorders. This application is directed to microRNA chips having a plurality of different oligonucleotides with specificity for genes associated with autism spectrum disorders. The invention is said to provide methods of identifying microRNA profiles for neurological and psychiatric conditions including autism spectrum disorders, methods of treating such conditions, and methods of identifying therapeutics for the treatment of such neurological and psychiatric conditions.

Yet another application is United States Patent Application Publication No. 2011/0159527, filed by Schlossmacher, et al., for Methods and Kits for Diagnosing Neurodegenerative Disease. Briefly, the application is said to teach methods and diagnostic kits for determining whether a subject may develop or be diagnosed with a neurodegenerative disease. The method is said to include quantitating the amount of alpha-synuclein and total protein in a cerebrospinal fluid (CSF) sample obtained from the subject and calculating a ratio of alpha-synuclein to total protein content; comparing the ratio of alpha-synuclein to total protein content in the CSF sample with the alpha-synuclein to total protein content ratio in CSF samples obtained from healthy neurodegenerative disease-free subjects; and determining from the comparison whether the subject has a likelihood to develop neurodegenerative disease or making a diagnosis of neurodegenerative disease in a subject. It is said that a difference in the ratio of alpha-synuclein to total protein content indicates that the subject has a likelihood of developing a neurodegenerative disease or has developed a neurodegenerative disease.

SUMMARY OF THE INVENTION

In one embodiment, the present invention includes a method and/or apparatus for screening for neurological disease within a primary care setting comprising: obtaining a blood test sample from a subject in the primary care setting; measuring two or more biomarkers in the blood sample selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein; comparing the level of the one or a combination of biomarkers with the level of a corresponding one or combination of biomarkers in a normal blood sample; measuring an increase in the level of the two or more biomarkers in the blood test sample in relation to that of the normal blood sample, which indicates that the subject is likely to have a neurological disease; identifying the neurological disease based on the two biomarkers measured; and selecting a course of treatment for the subject based on the neurological disease predicted. In one aspect, at least one of the biomarker measurements is obtained by a method selected from the group consisting of immunoassay and enzymatic activity assay. In another aspect, the method further comprises advising the individual or a primary health care practitioner of the change in calculated risk. In another aspect, the method further comprises advising the individual or a primary health care practitioner of the change in calculated risk. In another aspect, the method uses 3, 4, 5, 6, 7, 8, 9, 10, 11, 12, or 13 biomarkers to distinguish between neurological diseases. In another aspect, the isolated biological sample is serum or plasma. In another aspect, the sample is a serum sample and upon the initial determination of a neurological disease within the primary care clinic, providing that primary care provider with information regarding the specific type of specialist referral appropriate for that particular blood screen finding and directing the individual to a specialist for that neurological disease and treatment in accordance therewith. In another aspect, the neurological diseases are selected from Alzheimer's Disease, Parkinson's Disease, Down's syndrome, Frontotemporal dementia, Dementia with Lewy Bodies, and neurodegenerative disease. In another aspect, the method further comprises the step of refining the analysis by including the following parameters: patient age, and a neurocognitive screening tests, wherein the combination of two or more of our serum-based markers, age and the neurocognitive screening tests are at least 90% accurate in a primary care setting for the determination of Alzheimer's disease when compared to a control subject that does not have a neurological disease or disorder. In another aspect, the method further comprises the step of determining one or more of the following parameters: sleep disturbance (yes/no), visual hallucinations (yes/no), psychiatric/personality changes (yes/no), age, neurocognitive screening, and two or more of our serum-based markers for the accurate detection and discrimination between neurodegenerative diseases. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling. In another aspect, the method is used to screen for at least one of mild AD (CDR global score<=1.0) with an overall accuracy of 94, 95, 96, 97, 98, 99 or 100% (sensitivity (SN), specificity (SP) of (SN=0.94, SP=0.83)), or very early AD (CDR global score=0.5), with an overall accuracy of 91, 92, 93, 94, 95, 96, 97, 98, 99, or 100% (SN=0.97, SP=0.72). In another aspect, the method is used to screen in the primary setting used a higher specificity than sensitivity, wherein the specificity is in the range of 0.97 to 1.0, and the sensitivity is in the range of 0.80 to 1.0.

Another embodiment of the present invention includes a method and apparatus for distinguishing between one or more neurological disease states; the method comprising: obtaining from at least one biological sample isolated from an individual suspected of having a neurological disease measurements of biomarkers comprising the biomarkers IL-7 and TNFα; adding the age of the subject and the results from one or more neurocognitive screening tests from the subject (clock drawing, verbal fluency, list learning, sleep disturbances, visual hallucinations, behavioral disturbances, motor disturbances); calculating the individual's risk for developing the neurological disease from the output of a model, wherein the inputs to the model comprise the measurements of the two biomarkers, the subject's age and the results from one or more cognitive tests, and further wherein the model was developed by fitting data from a longitudinal study of a selected population of individuals and the fitted data comprises levels of the biomarkers, the subject's age and the results from one or more cognitive tests and neurological disease in the selected population of individuals; and comparing the calculated risk for the individual to a previously calculated risk obtained from at least one earlier sample from the individual. In one aspect, at least one of the biomarker measurements is obtained by a method selected from at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling. In another aspect, two or more of the methods for biomarker measurement are used to cross-validate the neurological disease. In another aspect, the method further comprises advising the individual or a health care practitioner of the change in calculated risk. In another aspect, the method further comprises advising the individual or a health care practitioner of the change in calculated risk. In another aspect, the biomarkers further comprise one or more biomarkers selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein. In another aspect, the method uses 3, 4, 5, 6, 7, 8, 9, 10, 11, 12, or 13 biomarkers to distinguish the neurological disease. In another aspect, the isolated biological sample is serum or plasma. In another aspect, the sample is a serum sample and upon the initial determination of a neurological disease, directing the individual to a specialist for that neurological disease. In another aspect, the neurological diseases are selected from Alzheimer's Disease, Down's syndrome, Frontotemporal dementia, Dementia with Lewy Bodies, Parkinson's Disease, and dementia. In another aspect, the method is used to exclude one or more neurological diseases selected from Alzheimer's Disease, Down's syndrome, Frontotemporal dementia, Dementia with Lewy Bodies, Parkinson's Disease, and dementia. In another aspect, the method is used to screen in the primary setting used a higher specificity than sensitivity, wherein the specificity is in the range of 0.97 to 1.0, and the sensitivity is in the range of 0.80 to 1.0.

In another embodiment, the present invention also includes a method of performing a clinical trial to evaluate a candidate drug believed to be useful in treating neurological diseases, the method comprising: (a) measuring an two or more biomarkers selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein from one or more blood samples obtained from patients suspected of having a neurological disease, the patient's age, and results from one or more neurocognitive screening tests of the patient; (b) administering a candidate drug to a first subset of the patients, and a placebo to a second subset of the patients; (c) repeating step (a) after the administration of the candidate drug or the placebo; and (d) determining if the candidate drug reduces the expression of the one or more biomarkers that is statistically significant as compared to any reduction occurring in the second subset of patients, wherein a statistically significant reduction indicates that the candidate drug is useful in treating the neurological disease. In another aspect, the method further comprises the steps of obtaining one or more additional blood samples from the patient after a predetermined amount of time and comparing the levels of the biomarkers from the one or more additional samples to determine disease progression. In another aspect, the method further comprises the steps of treating the patient for a pre-determined period of time, obtaining one or more additional blood samples from the patient after the predetermined amount of time and comparing the levels of the biomarkers from the one or more additional samples to determine disease progression.

In another embodiment, the present invention also includes a method of selecting subjects for a clinical trial to evaluate a candidate drug believed to be useful in treating neurological diseases, the method comprising: (a) measuring an two or more biomarker selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein in a blood samples obtained from the subject, the patient's age and the results from one or more neurocognitive screening tests to determine a neurodegenerative disease profile; and (b) determining if the subject should participate in the clinical trial based on the results of the identification of the neurodegenerative disease profile of the subject obtained from the step (a), wherein the subject is only selected if the neurodegenerative disease profile if the candidate drug is likely to be useful in treating the neurological disease.

In another embodiment, the present invention also includes a method of evaluating the effect of a treatment for a neurological disease, the method comprising: treating a patient for a neurological disease; measuring two or more biomarkers from a blood samples obtained from patients suspected of having a neurological disease, the patient's age, and results from one or more cognitive tests of the patient; and determining if the treatment reduces the expression of the one or more biomarkers that is statistically significant as compared to any reduction occurring in the second subset of patients that have not been treated or from a prior sample obtained from the patient, wherein a statistically significant reduction indicates that the treatment is useful in treating the neurological disease.

In another embodiment, the present invention also includes a method of aiding diagnosis of neurological diseases, comprising: obtaining a blood sample from a human individual; comparing normalized measured levels of IL-7 and TNFα biomarkers from the individual's blood sample to a reference level of each neurological disease diagnosis biomarker; wherein the group of neurological disease diagnosis biomarkers comprises IL-7 and TNFα; and obtaining the patient's age and results from one or more cognitive tests of the patient; wherein the reference level of each neurological disease diagnosis biomarker comprises a normalized measured level of the neurological disease diagnosis biomarker from one or more blood samples of human individuals without neurological disease; and wherein levels of neurological disease diagnosis biomarkers greater than the reference level of each neurological disease diagnosis biomarker, the patient's age and the patient's results from one or more cognitive tests indicate a greater likelihood that the individual suffers from neurological disease. In one aspect, the present invention also includes a method of level of expression of IL-7 and TNF alpha in the blood are elevated when compared to the reference level indicates a greater likelihood that the individual suffers from the neurological disease. In another aspect, the method further comprises the step of determining the blood levels of one or more biomarkers selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein. In another aspect, the method uses 3, 4, 5, 6, 7, 8, 9, 10, 11, 12, or 13 biomarkers to distinguish the neurological disease. In another aspect, the levels of CRP and IL10 are lower when compared to the reference level indicates a greater likelihood that the individual suffers from the neurological disease. In another aspect, the method further comprises the steps of obtaining one or more additional blood samples from the patient after a predetermined amount of time and comparing the levels of the biomarkers from the one or more additional samples to determine disease progression. In another aspect, the isolated blood sample is serum sample. In another aspect, the blood sample is a serum sample and upon the initial determination of a neurological disease, directing the individual to a specialist for that neurological disease. In another aspect, the neurological diseases are selected from Alzheimer's Disease, Parkinson's Disease, and dementia. In another aspect, the method is used to screen in the primary setting used a higher specificity than sensitivity, wherein the specificity is in the range of 0.97 to 1.0, and the sensitivity is in the range of 0.80 to 1.0.

In another embodiment, the present invention also includes a rapid-screening kit for aiding diagnosis of a neurological disease in a primary care setting, comprising: one or more reagents for detecting the level of expression of IL-7 and TNFα in a blood sample obtained from a human individual, and one or more neurological screening test sheets; and instructions for comparing normalized measured levels of the IL-7 and TNFα biomarkers from the individual's blood sample to a reference level, the patient's age and the patient's results from the neurological screening tests; wherein the reference level of each neurological disease diagnosis biomarker comprises a normalized measured level of the neurological disease diagnosis biomarker from one or more blood samples of human individuals without neurological disease; and wherein levels of neurological disease diagnosis biomarkers less than the reference level of each neurological disease diagnosis biomarker indicate a greater likelihood that the individual suffers from neurological disease, wherein the test is at least 90% accurate. In another aspect, the level of expression of IL-7 and TNF alpha in the blood are elevated when compared to the reference level indicates a greater likelihood that the individual suffers from the neurological disease. In another aspect, the kit further comprises one or more reagents for detecting the level of expression markers selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein. In another aspect, the levels of CRP and IL10 are lower when compared to the reference level indicates a greater likelihood that the individual suffers from the neurological disease. In another aspect, the sample is a serum sample and upon the initial determination of a neurological disease, directing the individual to a specialist for that neurological disease. In another aspect, the neurological diseases are selected from Alzheimer's Disease, Down's syndrome, Frontotemporal dementia, Dementia with Lewy Bodies, Parkinson's Disease, and dementia. In another aspect, the level of expression of the various proteins is measured at least one of the nucleic acid, the protein level, or functionally at the protein level. In another aspect, the level of expression of the various proteins is measured by at least one of fluorescence detection, chemiluminescence detection, electrochemiluminescence detection and patterned arrays, reverse transcriptase-polymerase chain reaction, antibody binding, fluorescence activated sorting, detectable bead sorting, antibody arrays, microarrays, enzymatic arrays, receptor binding arrays, allele specific primer extension, target specific primer extension, solid-phase binding arrays, liquid phase binding arrays, fluorescent resonance transfer, or radioactive labeling.

In another embodiment, the present invention also includes a method of determining one or more neurological disease profiles that best matches a patient profile, comprising: (a) comparing, on a suitably programmed computer, the level of expression of IL-7 and TNFα in a blood sample from a patient suspected of having one or more neurological diseases with reference profiles in a reference database to determine a measure of similarity between the patient profile and each the reference profiles; (b) identifying, on a suitably programmed computer, a reference profile in a reference database that best matches the patient profile based on a maximum similarity among the measures of similarity determined in step (a); and (c) outputting to a user interface device, a computer readable storage medium, or a local or remote computer system; or displaying, the maximum similarity or the disease of the disease cell sample of the reference profile in the reference database that best matches the patient profile. In one aspect, the method further comprises the step of determining the level of expression of one or more markers from a blood sample selected from IL7, TNFα, IL5, IL6, CRP, IL10, TNC, ICAM1, FVII, I309, TNFR1, A2M, TARC, eotaxin3, VCAM1, TPO, FABP, IL18, B2M, SAA, PPY, DJ1, and/or α-synuclein. In another aspect, the method uses 3, 4, 5, 6, 7, 8, 9, 10, 11, 12, or 13 biomarkers to distinguish the neurological disease. In another aspect, the method is used to screen in the primary setting used a higher specificity than sensitivity, wherein the specificity is in the range of 0.97 to 1.0, and the sensitivity is, in the range of 0.80 to 1.0.

BRIEF DESCRIPTION OF THE DRAWINGS

For a more complete understanding of the features and advantages of the present invention, reference is now made to the detailed description of the invention along with the accompanying figures and in which:

FIG. 7 shows the selection of the specialist for referral, and hence the course of treatment, based on the results of the screen of the two or more biomarkers measured at the primary care center or point of care.

DESCRIPTION OF THE INVENTION

Figure 1:
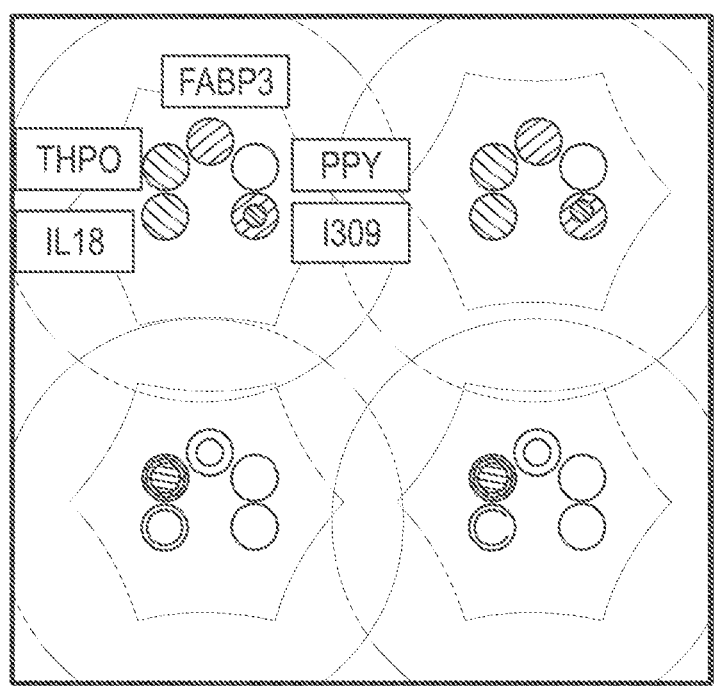
FIG. 1 shows data from the Neurodegenerative Panel 1 that assays THPO, FABP3, PPY, IL18, and I309 on an MSD platform from two control participants in duplicate. As can be seen, the assays are highly reliable.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the phrase "primary care clinic", "primary care setting", "primary care provider" are used interchangeably to refer to the principal point of contact/consultation for patients within a health care system and coordinates with specialists that the patient may need.

As used herein, the phrase "specialist" refers to a medical practice or practitioner that specializes in a particular disease, such as neurology, psychiatry or even more specifically movement disorders or memory disorders.

As used herein, the following abbreviations are used and can include mammalian version of these genes but in certain embodiments the genes are human genes: IL7—interleukin-7, TNFα—tumor necrosis factor alpha, IL5—interleukin-5, IL6—interleukin-6, CRP— C-reactive protein, IL10—interleukin-10, TNC—Tenascin C, ICAM1—intracellular adhesion molecule 1, FVII—factor VII, I309—chemokine (C-C motif) ligand 1, TNFR1—tumor necrosis factor receptor 1, A2M—alpha-2-microglobulin, TARC—Chemokine (C-C Motif) Ligand 17, eotaxin3, VCAM1—Vascular Cell Adhesion Molecule 1, TPO—thyroid peroxidase, FABP3—fatty acid binding protein 3, IL18-interleukin-18, B2M—beat-2-microglobulin, SAA—serum amyloid A1 cluster, PPY—pancreatic polypeptide, DJ1—Parkinson Protein 7, α-synuclein.

As used herein, the phrase "neurological disease" refers to a disease or disorder of the central nervous system and many include, e.g., neurodegenerative disorders such as AD, Parkinson's disease, mild cognitive impairment (MCI) and dementia and neurological diseases include multiple sclerosis, neuropathies. The present invention will find particular use in detecting AD and for distinguishing the same, as an initial or complete screen, from other neurodegenerative disorders such as Parkinson's Disease, Frontotemporal dementia, Dementia with Lewy Bodies, and Down's syndrome. As used herein, the terms "Alzheimer's patient", "AD patient", and "individual diagnosed with AD" all refer to an individual who has been diagnosed with AD or has been given a probable diagnosis of Alzheimer's Disease (AD).

As used herein, the terms "Parkinson's disease patient", and "individual diagnosed with Parkinson's disease" all refer to an individual who has been diagnosed with PD or has been given a diagnosis of Parkinson's disease.

As used herein, the terms "Frontotemporal dementia", and "individual diagnosed with frontotemporal dementia" all refer to an individual who has been diagnosed with FTD or has been given a diagnosis of FTD.

As used herein, the term "Dementia with Lewy bodies" (DLB), and "individual diagnosed with DLB" all refer to an individual who has been diagnosed with DLB or has been given a diagnosis of DLB.

As used herein, the term "Down's syndrome" (DS), and "individual diagnosed with Down's syndrome" all refer to an individual who has been diagnosed with DS or has been given a diagnosis of DS.

As used herein, the phrase "neurological disease biomarker" refers to a biomarker that is a neurological disease diagnosis biomarker.

As used herein, the term "neurological disease biomarker protein", refers to any of: a protein biomarkers or substances that are functionally at the level of a protein biomarker.

As used herein, methods for "aiding diagnosis" refer to methods that assist in making a clinical determination regarding the presence, or nature, of the neurological disease (e.g., AD, PD, DLB, FTD, DS or MCI), and may or may not be conclusive with respect to the definitive diagnosis. Accordingly, for example, a method of aiding diagnosis of neurological disease can comprise measuring the amount of one or more neurological disease biomarkers in a blood sample from an individual.

As used herein, the term "stratifying" refers to sorting individuals into different classes or strata based on the features of a neurological disease. For example, stratifying a population of individuals with Alzheimer's disease involves assigning the individuals on the basis of the severity of the disease (e.g., mild, moderate, advanced, etc.).

As used herein, the term "predicting" refers to making a finding that an individual has a significantly enhanced probability of developing a certain neurological disease.

As used herein, "biological fluid sample" refers to a wide variety of fluid sample types obtained from an individual and can be used in a diagnostic or monitoring assay. Biological fluid sample include, e.g., blood, cerebral spinal fluid (CSF), urine and other liquid samples of biological origin. Commonly, the samples are treatment with stabilizing reagents, solubilization, or enrichment for certain components, such as proteins or polynucleotides, so long as they do not interfere with the analysis of the markers in the sample.

As used herein, a "blood sample" refers to a biological sample derived from blood, preferably peripheral (or circulating) blood. A blood sample may be, e.g., whole blood, serum or plasma. In certain embodiments, serum is preferred as the source for the biomarkers as the samples are readily available and often obtained for other sampling, is stable, and requires less processing, thus making it ideal for locations with little to refrigeration or electricity, is easily transportable, and is commonly handled by medical support staff.

As used herein, a "normal" individual or a sample from a "normal" individual refers to quantitative data, qualitative data, or both from an individual who has or would be assessed by a physician as not having a disease, e.g., a neurological disease. Often, a "normal" individual is also age-matched within a range of 1, 2, 3, 4, 5, 6, 7, 8, 9 or 10 years with the sample of the individual to be assessed.

As used herein, the term "treatment" refers to the alleviation, amelioration, and/or stabilization of symptoms, as well as delay in progression of symptoms of a particular disorder. For example, "treatment" of AD includes any one or more of: (1) elimination of one or more symptoms of AD, (2) reduction of one or more symptoms of AD, (3) stabilization of the symptoms of AD (e.g., failure to progress to more advanced stages of AD), and (4) delay in onset of one or more symptoms of AD delay in progression (i.e., worsening) of one or more symptoms of AD; and (5) delay in progression (i.e., worsening) of one or more symptoms of AD.

As used herein, the term "fold difference" refers to a numerical representation of the magnitude difference between a measured value and a reference value, e.g., an AD biomarker, a Parkinson's biomarker, a dementia biomarker, or values that allow for the differentiation of one or more of the neurological diseases. Typically, fold difference is calculated mathematically by division of the numeric measured value with the numeric reference value. For example, if a measured value for an AD biomarker is 20 nanograms/milliliter (ng/ml), and the reference value is 10 ng/ml, the fold difference is 2 (20/10=2). Alternatively, if a measured value for an AD biomarker is 10 nanograms/milliliter (ng/ml), and the reference value is 20 ng/ml, the fold difference is 10/20 or −0.50 or −50%).

As used herein, a "reference value" can be an absolute value, a relative value, a value that has an upper and/or lower limit, a range of values; an average value, a median value, a mean value, or a value as compared to a particular control or baseline value. Generally, a reference value is based on an individual sample value, such as for example, a value obtained from a sample from the individual with e.g., a neurological disease such as AD, Parkinson's Disease, or dementia, preferably at an earlier point in time, or a value obtained from a sample from an neurological disease patient other than the individual being tested, or a "normal" individual, that is an individual not diagnosed with AD, Parkinson's Disease, or dementia. The reference value can be based on a large number of samples, such as from AD patients, Parkinson's Disease patients, dementia patients, or normal individuals or based on a pool of samples including or excluding the sample to be tested.

As used herein, the phrase "a predetermined amount of time" is used to describe the length of time between measurements that would yield a statistically significant result, which in the case of disease progression for neurological disease can be 7 days, 2 weeks, one month, 3 months, 6 months, 9 months, 1 year, 1 year 3 months, 1 year 6 months, 1 year 9 months, 2 years, 2 years 3 months, 2 years 6 months, 2 years 9 months, 3, 4, 5, 6, 7, 8, 9 or even 10 years and combinations thereof.

As used herein, the phrases "neurocognitive screening tests", or "cognitive test" are used to describe one or more tests known to the skilled artisan for measuring cognitive status or impairment and can include but is not limited to: a 4-point clock drawing test, an verbal fluency test, trail making test, list learning test, and the like. The skilled artisan will recognize and know how these tests can be modified, how new tests that measure similar cognitive function can be developed and implemented for use with the present invention.

The differential diagnosis of neurodegenerative diseases is difficult, yet of critical importance for clinical treatment and management as well as for designing therapeutic and prevention trials[1-4]. In order for patients to be referred to specialty clinics for advanced assessments and treatment implementation, an appropriate referral is normally required from primary care providers. However, prior work demonstrates that the assessment and management of neurodegenerative diseases is poor in primary care settings[5-8] with inappropriate medications frequently administered[9]. Given that the average physician visit duration in an ambulatory setting for those age 65+ is approximately 18 minutes[10], primary care providers are in desperate need for a rapid and cost-effective method for screening neurological illness within their geriatric patients so appropriate referrals to a specialist can be made as warranted.

The availability of blood-based screening tools that can be implemented within primary care clinic settings has significant implications. From a clinical standpoint, while fewer than half of physicians surveyed believed screenings for neurodegenerative disease was important, the vast majority of the general public and caregivers believed such screenings were vitally important[11]. Additionally, the average physician visit is less than 20 minutes for elderly patients in an ambulatory setting[10], severely limiting the time available for even brief neurological and cognitive assessments. Therefore, primary care providers are in desperate need of a method for determining which patients should be referred to a specialist for advanced clinical evaluation of possible neurodegenerative disease. While a tremendous amount of work has been completed demonstrating the utility of advanced neuroimaging techniques (MRI, fMRI, DTI, PET) in diagnosing neurodegenerative diseases, they are cost prohibitive as the first step in a multi-stage diagnostic process. Due to cost and access, it has been proposed that blood-based biomarkers "will most likely be the prerequisite to future sensitive screening of large populations" at risk for neurodegenerative disease and the baseline in a diagnostic flow approach[12]. For example, PET amyloid-beta (Aβ) scans were recently FDA approved for use in the diagnostic process of Alzheimer's disease. If PET Aβ imaging were made available at even $1,000 per exam (less than a third to one tenth of the actual cost) and only 1 million elders were screened annually within primary care settings (there are 40 million Americans age 65+), the cost would be $1 billion (U.S. dollars) annually for neurodegenerative screening. If a blood-based screener were made available at $100/person, the cost would be $100 million annually. If 15% tested positive and went on to PET Aβ imaging ($150 million), the cost savings of this screen—follow-up procedure would be $750 million dollars annually screening less than one fortieth of those who actually need annual screening.

A blood-based tool can easily fit the role as the first step in the multi-stage diagnostic process for neurodegenerative diseases with screen positives being referred to specialist for confirmatory diagnosis and treatment initiation. In fact, this is the process already utilized for the medical fields of cancer, cardiology, infectious disease and many others.

While application of specialty clinic-based screens to primary care settings seems straight forward, this is not the case and no prior procedures will work within primary care settings as demonstrated below. The ability to implement blood-based screenings as the first step in a multi-stage diagnostic process is critical, yet very complicated due to substantially lower base rates of disease presence as compared to specialty clinics[13] and this lower base rate has a tremendous impact on the predictive accuracy of test results.

Another substantial advancement comes from the current procedure. Specifically, the procedure can also be utilized for screening patients prior to entry into a clinical trial. A major impediment to therapeutic trials aimed at preventing, slowing progression, and/or treating AD is the lack of biomarkers available for detecting the disease[14,15]. The validation of a blood-based screening tool for AD could significantly reduce the costs of such trials by refining the study entry process. If imaging diagnostics (e.g., Aβ neuroimaging) are required for study entry, only positive screens on the blood test would be referred for the second phase of screening (i.e., PET scan), which would drastically reduce the cost for identification and screening of patients. The new methods for screening of the present invention facilitate recruitment, screening, and/or selection of patients from a broader range of populations and/or clinic settings, thereby offering underserved patient populations the opportunity to engage in clinical trials, which has been a major limitation to the majority of previously conducted trials[16].

The present inventors provide for the first time, data that demonstrates the following: a novel procedure can detect and discriminate between neurodegenerative diseases with high accuracy. The current novel procedure which can be utilized for implementation as the first line screen within primary care settings that leads to specific referrals to specialist providers for disease confirmation and initiation of treatment.

Methods. Neurodegenerative disease patients. AD and Control Patients. Non-fasting serum samples from the 300 TARCC participants (150 AD cases, 150 controls) were analyzed. Additionally, 200 plasma samples (100 AD cases and 100 controls), from the same subject group were analyzed. The methodology of the TARCC protocol has been described elsewhere[21,22]. Briefly, each participant undergoes an annual standardized assessment at one of the five participating TARCC sites that includes a medical evaluation, neuropsychological testing, and a blood draw. Diagnosis of AD is based on NINCDS-ADRDA criteria[23] and controls performed within normal limits on psychometric testing. Institutional Review Board approval was obtained at each site and written informed consent is obtained for all participants.

Non-AD Patients. Down's Samples. Serum samples were obtained from 11 male patients diagnosed with Down's syndrome (DS) from the Alzheimer's Disease Cooperative Studies core at the University of California San Diego (UCSD). Parkinson's disease Samples. Serum samples from 49 patients (28 males and 21 females) diagnosed with Parkinson's disease (PD) came from the University of Texas Southwestern Medical Center (UTSW) Movement Disorders Clinic. Dementia with Lewy Bodies (DLB) and Frontotemporal dementia (FTD) Samples. Serum samples from 11 DLB and 19 FTD samples were obtained from the UTSW Alzheimer's Disease Coordinating Center (ADCC).

Serum sample collection. TARCC and UTSW ADC serum samples were collected as follows: (1) non-fasting serum samples was collected in 10 ml tiger-top tubes, (2) allowed to clot for 30 minutes at room temperature in a vertical position, (3) centrifuged for 10 minutes at 1300×g within one hour of collection, (4) 1.0 ml aliquots of serum were transferred into cryovial tubes, (5) Freezerworks™ barcode labels were firmly affixed to each aliquot, and (6) samples placed into −80° C. freezer for storage until use in an assay. Down's syndrome serum samples were centrifuged at 3000 rpm for 10 minutes prior to aliquoting and storage in a −80° C. freezer.

Plasma: (1) non-fasting blood was collected into 10 ml lavender-top tubes and gently invert 10-12 times, (2) centrifuge tubes at 1300×g for 10 minutes within one hour of collection, (3) transfer 1 ml aliquots to cryovial tubes, (4) affix Freezerworks™ barcode labels, and (5) placed in −80° C. freezer for storage.

Human serum assays. All samples were assayed in duplicate via a multi-plex biomarker assay platform using electrochemiluminescence (ECL) on the SECTOR Imager 2400A from Meso Scale Discovery (MSD; www.mesoscale.com). The MSD platform has been used extensively to assay biomarkers associated with a range of human disease including AD[24-28]. ECL technology uses labels that emit light when electrochemically stimulated, which improves sensitivity of detection of many analytes at very low concentrations. ECL measures have well-established properties of being more sensitive and requiring less volume than conventional ELISAs[26], the gold standard for most assays. The markers assayed were from a previously generated and cross-validated AD algorithm[17,19,29] and included: fatty acid binding protein (FABP3), beta 2 microglobulin, pancreatic polypeptide (PPY), sTNFR1, CRP, VCAM1, thrombopoeitin (THPO), α2 macroglobulin (A2M), exotaxin 3, tumor necrosis factor α, tenascin C, IL-5, IL6, IL7, IL10, IL18, I309, Factor VII, TARC, SAA, and ICAM1. FIG. 1 illustrates the reliability of the MSD assay of the present invention.

Statistical Analyses. Analyses were performed using R (V 2.10) statistical software[30] and IBM SPSS19. Chi square and t-tests were used to compare case versus controls for categorical variables (APOE ε4 allele frequency, gender, race, ethnicity, presence of cardiovascular risk factors) and continuous variables (age, education, Mini Mental State Exam [MMSE] and clinical dementia rating sum of boxes scores [CDR-SB]), respectively. The biomarker data was transformed using the Box-Cox transformation. The random forest (RF) prediction model was performed using R package randomForest (V 4.5)[31], with all software default settings. The ROC (receiver operation characteristic) curves were analyzed using R package AUC (area under the curve) was calculated using R package DiagnosisMed (V 0.2.2.2). The sample was randomly divided into training and test samples separately for serum and plasma markers. The RF model was generated in the training set and then applied to the test sample. Logistic regression was used to combine demographic data (i.e. age, gender, education, and APOE4 presence [yes/no]) with the RF risk score as was done in the present inventors' prior work[17,19,29,32]. Clinical variables were added to create a more robust diagnostic algorithm given the prior work documenting a link between such variables and cognitive dysfunction in AD[33-36]. In order to further refine the algorithm, the biomarker risk score was limited to the smallest set of markers that retained optimal diagnostic accuracy as a follow-up analysis. For the second aim of these studies, support vector machines (SVM) analysis was utilized for multi-classification of all diagnostic groups. A random sample of data from 100 AD cases and controls utilized in the first set of analyses (AD n=51; NC n=49) was selected and combined with serum data from 11 DS, 49 PD, 19 FTD and 11 DLB cases along with 12 additional normal controls (NC) (62 total NCs). The SVM analyses were run on the total combined sample with five-fold cross-validation. SVM is based on the concept of decision planes that define decision boundaries and is primarily a method that performs classification tasks by constructing hyperplanes in a multidimensional space that separates cases of different class labels. An SVM-based method was used with five-fold cross-validation to develop the classifier for the combined samples, and then applied the classifier to predict the combined samples.

Results. As with prior work from the present inventors, the AD patients were significantly older (p<0.001), achieved fewer years of education (p<0.001), scored lower on the MMSE (p<0.001) and higher on the CDR-SB (p<0.001) (see Table 1). There was no significant difference between groups in terms of gender or presence of dyslipidemia, diabetes, or hypertension. The AD group had significantly more APOE4 carriers while the NC group had significantly more individuals who were classified as obese (BMI>=30).

TABLE 1

Demographic Characteristics of Cohort

|  | AD (N = 150) | Control (N = 150) | P-value |
|---|---|---|---|
| Gender (male) | 35% | 31% | 0.46 |
| Age (years) | 78.0 (8.2) | 70.6 (8.9) | <0.001 |
|  | 57-94 | 52-90 |  |
| Education (years) | 14.0 (3.4) | 15.6( 2.7) | <0.001 |
|  | 0-22 | 10-23 |  |

TABLE 1-continued

Demographic Characteristics of Cohort

|  | AD (N = 150) | Control (N = 150) | P-value |
|---|---|---|---|
| APOE4 presence (yes/no) | 61% | 26% | <0.001 |
| Hispanic Ethnicity | 5% | 5% | 0.61 |
| Race (non-Hispanic white) | 95% | 97% | 0.49 |
| MMSE | 19.2(6.1) | 29.4 (0.9) | <0.001 |
|  | 1-30 | 26-30 |  |
| CDR-SB | 7.8 (4.4) | 0.0 (0.04) | <0.001 |
|  | 1-18 | 0-1 |  |
| Hypertension (% yes) | 56% | 59% | 0.73 |
| Dyslipidemia (% yes) | 53% | 56% | 0.49 |
| Diabetes (% yes) | 12% | 13% | 0.60 |
| Obese (% yes) | 13% | 24% | 0.04 |

Figure 2:
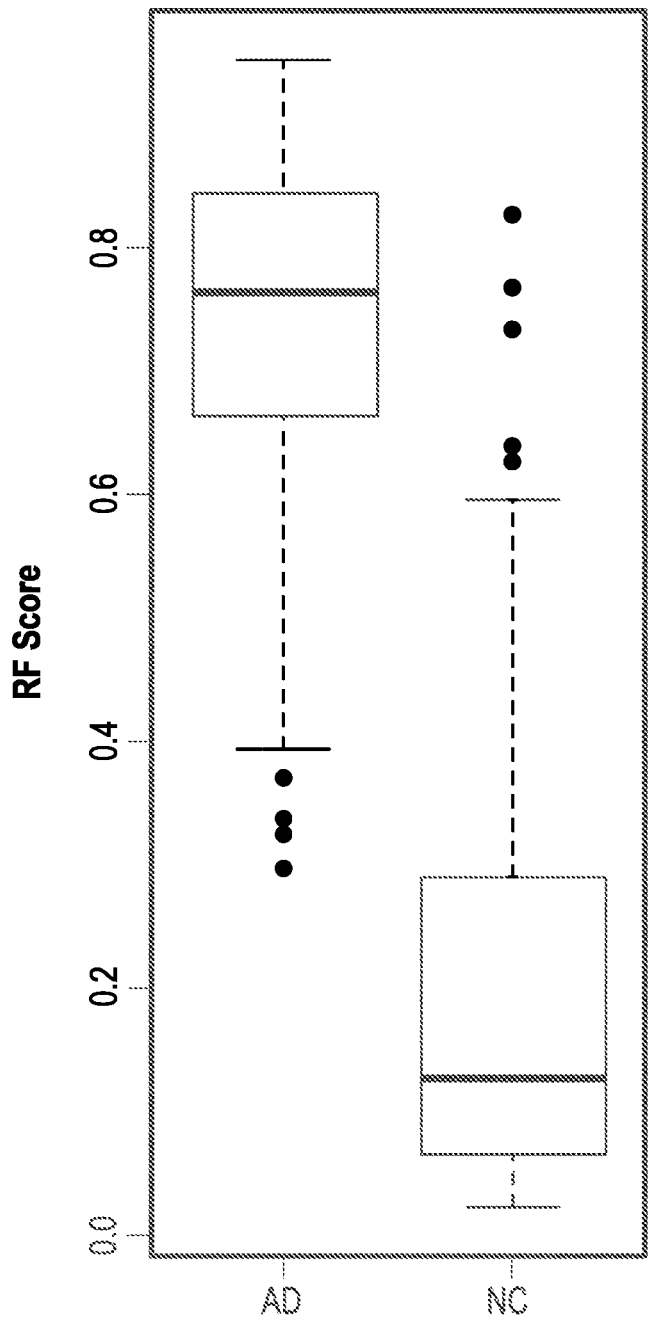
FIG. 2 is a box Plot of Random Forest Risk Scores for AD vs. normal controls (NC)
Figure 3:
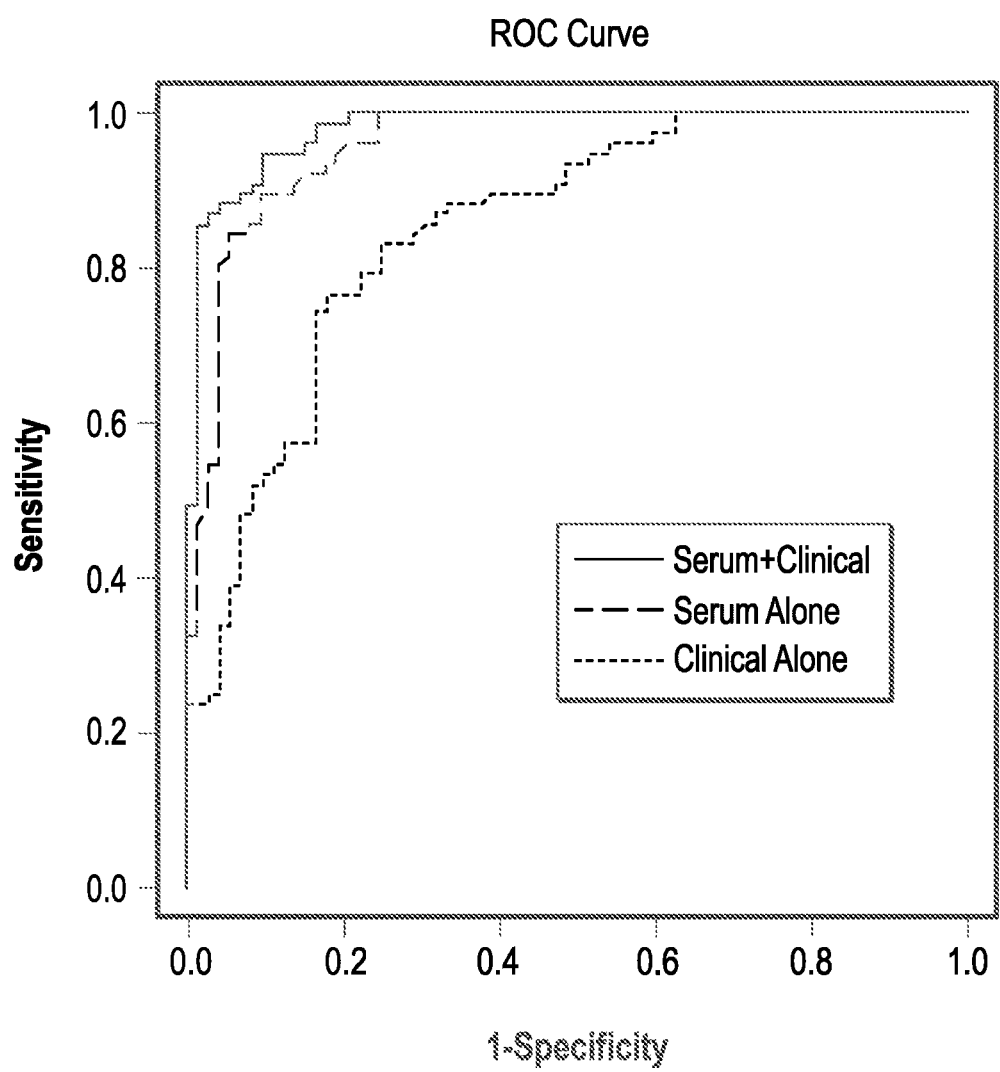
FIG. 3 is a receiver operation characteristic (ROC) plot of serum biomarker profile.

When the serum-based RF biomarker profile from the ECL assays was applied to the test sample, the obtained sensitivity (SN) was 0.90, specificity (SP) was 0.90 and area under the ROC curve (AUC) was 0.96 (See FIGS. 2 and 3, and Table 2).

TABLE 2

Statistical results for AD biomarker sensitivity and specificity and area under the receiver operating characteristic curve (AUC).

|  | AUC | Sensitivity (95% CI) | Specificity (95% CI) |
|---|---|---|---|
| Serum Biomarker alone | 0.96 | 0.90 (0.81, 0.95) | 0.90 (0.82, 0.95) |
| Clinical variables alone | 0.85 | 0.77 (0.66, 0.85) | 0.82 (0.72, 0.89) |
| Biomarkers + Clinical variables | 0.98 | 0.95 (0.87, 0.98) | 0.90 (0.81, 0.95) |
| Abbreviated Biomarker Profile (8 proteins) | 0.95 | 0.88 (0.79, 0.94) | 0.92 (0.83, 0.96) |
| Abbreviated Biomarker Profile (8 proteins) + Clinical Variables | 0.98 | 0.92 (0.84, 0.96) | 0.94 (0.87, 0.98) |
| Plasma Biomaker alone | 0.76 | 0.65 (0.46, 0.74) | 0.790.69, 0.95) |

FIG. 3 shows a ROC plot for a serum biomarker profile using 21 serum biomarkers. The plasma-based algorithm yielded much lower accuracy estimates of SN, SP, and AUC of 0.65, 0.79, and 0.76, respectively. Therefore, the remaining analyses focused solely on serum. Inclusion of age, gender, education and APOE4 into the algorithm with the RF biomarker profile increased SN, SP, and AUC to 0.95, 0.90, and 0.98, respectively (Table 2). Next the RF was re-run to determine the optimized algorithm with the smallest number of serum biomarkers. Using only the top 8 markers from the biomarker profile (see FIG. 4) yielded a SN, SP, and AUC of 0.88, 0.92 and 0.95, respectively (see FIG. 5 and Table 2). The addition of age, gender, education and APOE4 genotype increased SN, SP, and AUC to 0.92, 0.94, and 0.98, respectively.

Figure 4:
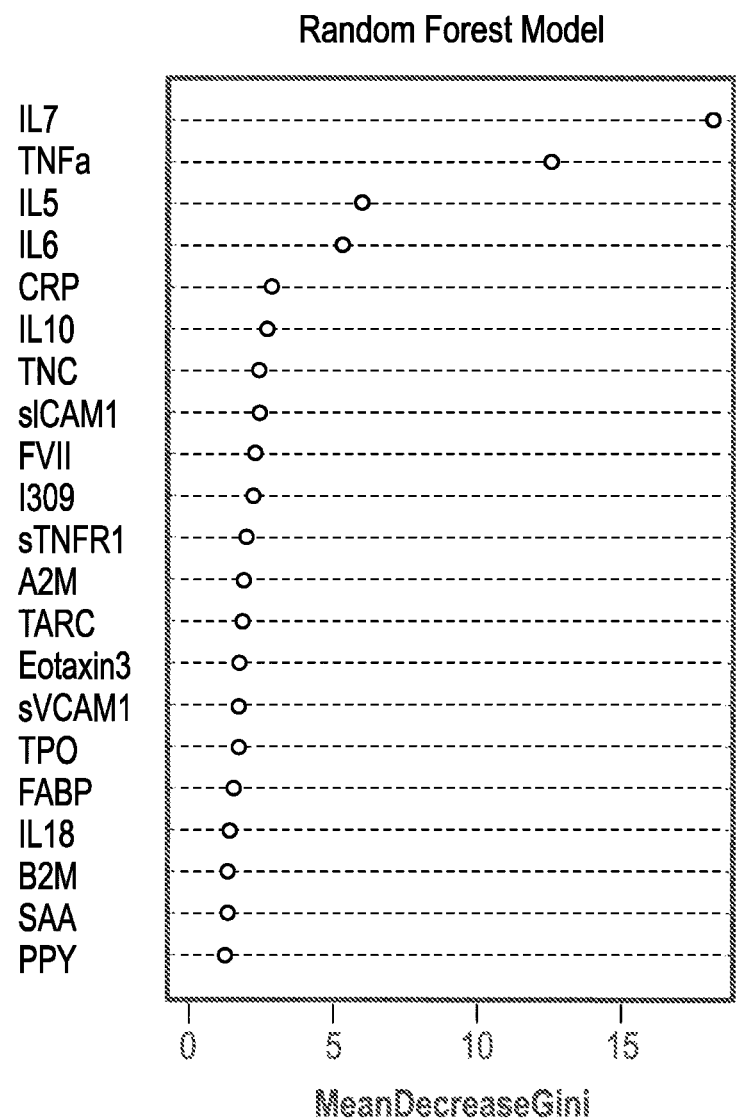
FIG. 4 is a Gini Plot from Random Forest Biomarker Model.
Figure 5:
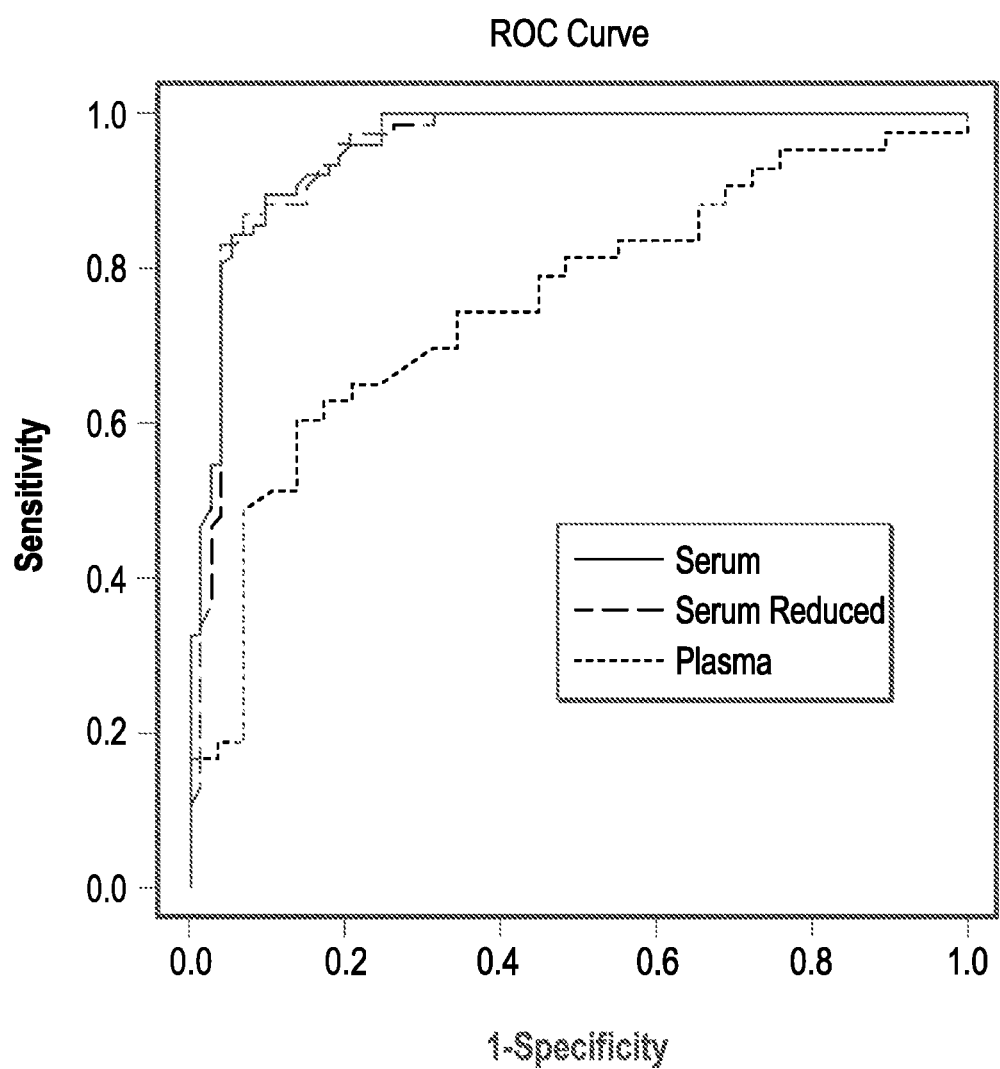
FIG. 5 is a receiver operation characteristic (ROC) plot of serum biomarker profile.

FIG. 4 shows a Gini Plot from Random Forest Biomarker Model demonstrating variable importance and differential expression. FIG. 5 shows a ROC plot using only the top 8 biomarkers for the AD algorithm.

For the SVM multi-classifier analyses to determine if the AD blood-based biomarker profiles could be utilized to discriminate AD from other neurological diseases, analyses were conducted on protein assays from 203 participants (AD n=51, PD n=49, DS n=11, FTD n=19, DLB n=11, NC n=62). Demographic characteristics of this sample are provided in Table 3.

TABLE 3

Demographic characteristics of a second cohort for multivariate classification

|  | AD N = 51 | PD N = 49 | DS N = 11 | FTD N = 19 | DLB N = 11 | NC N = 61 |
|---|---|---|---|---|---|---|
| Age | 78.0 (9.0) | 68 (9.6) | 52 (2.0) | 65.8 (8.8) | 75.6 (4.5) | 70 (9.0) |
| Education | 15.0 (3.0) | — | — | 14.8 (3.2) | 14.8 (2.8) | 16.2 (2.7) |
| Gender | 22 M; 29 F | 28 M; 21 F | 52 M | 14 M; 5 F | 8 M; 3 F | 23 M; 38 F |

Note:
information not available regarding education for PD and DS cases.
Abbreviations:
AD, Alzheimer's disease.
PD, Parkinson's disease.
DS, Down's syndrome.
FTD, Frontotemporal dementia.
DLB, Lewy Body dementia.
NC, normal controls.

Figure 6:
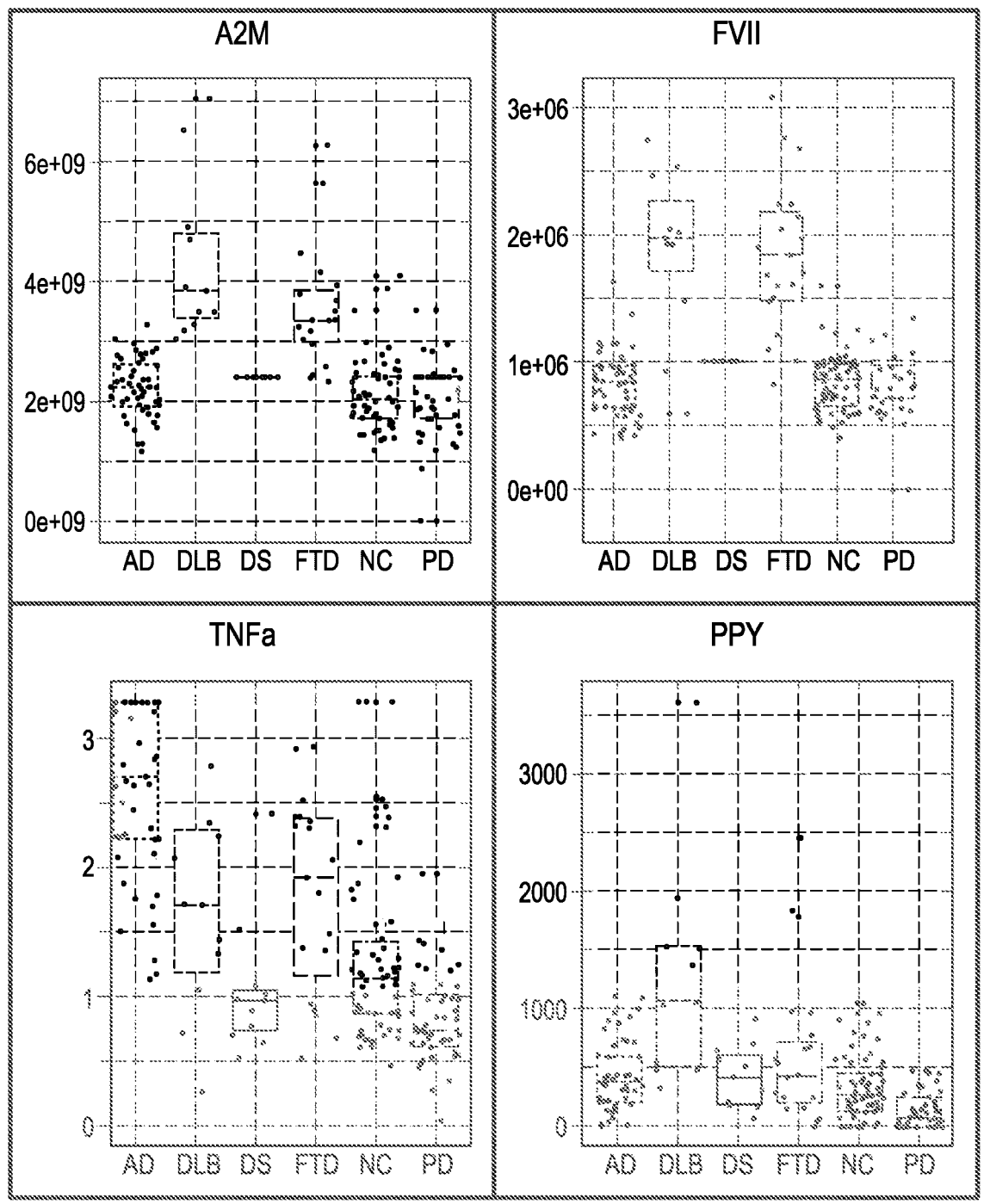
FIG. 6 highlights the importance of the relative profiles in distinguishing between neurodegenerative diseases. The relative profiles across disease states varied.

FIG. 6 highlights the importance of the relative profiles in distinguishing between neurodegenerative diseases. The relative profiles across disease states varied. For example, A2M and FVII are disproportionately elevated in DLB and FTD whereas TNFα is disproportionately elevated in AD and lowest in PD and DLB whereas PPY is lowest in PD and highest in DLB. Using the SVM-based algorithm, biomarker profiles combining all proteins were created to simultaneously classify all participants. Surprisingly, the overall accuracy of the SVM was 100% (SN=1.0, SP=1.0) with all of the individuals being correctly classified within their respective categorizations.

Implementing the blood screen in a community-based setting. The 1998 Consensus Report of the Working Group on: "Molecular and Biochemical Markers of Alzheimer's Disease"[37] provided guidelines regarding the minimal acceptable performance standards of putative biomarkers for AD. It was stated that sensitivity (SN) and specificity (SP) should be no less than 0.80 with positive predictive value (PPV) of 80% or more, with PPV approaching 90% being best. The report also states that a "high negative predictive value [NPV] would be extremely useful." The PI and bioinformatics team on this grant have extensive experience calculating diagnostic accuracy statistics, including PPV and NPV[17-20,38-43]. The important difference between SN/SP and PPV/NPV is that the latter are prediction accuracy statistics (i.e. how correct is a clinician when diagnosing a patient based on the test). PPV/NPV are dependent on base rates of disease presence[44]. With regards to AD, it is estimated that the base rate of disease presence in the community is 11% of those age 65 and above[13] as compared to 50% or more in specialty clinic settings. PPV and NPV are based on Bayesian statistics and calculated as outlined here:

$$PPV = \frac{(SN \times BR)}{(SN \times BR) + [(1 - SP) \times RC]}$$

$$NPV = \frac{(SP \times RC)}{(SP \times RC) + [(1 - SN) \times BR]}$$

PPV=positive predictive value, SN=sensitivity, BR=base rate, RC=remaining cases, NPV=negative predictive value, SP=specificity. In an 8-protein screen or algorithm, when SP was held at 0.98, SN fell to 0.86. Applying PPV and NPV calculations with an estimated base rate of AD of 11% within the community[13], the screen and/or algorithm of the present invention is very accurate and can be used within a community-based setting, that is, at the primary point-of-care. This is in comparison to the minimal requirements to be acceptable based on the 1998 Consensus Report where PPV was less than 35% (see Table 4).

TABLE 4

Diagnostic Accuracy of Blood-Based Screen for Alzheimer's disease in Primary Care Settings

| | | | Base Rate = 11% | |
|---|---|---|---|---|
| | SN | SP | PPV | NPV |
| Current Novel Procedure | 0.86 | 0.98 | 0.84 | 0.98 |
| 1998 Consensus Report minimal guidelines[37] | 0.80 | 0.80 | 0.33 | 0.97 |
| Our Prior work[17] | 0.94 | 0.84 | .42 | .99 |
| Our Prior work[18] | 0.89 | 0.85 | 0.42 | 0.98 |
| Our Prior work[19] | 0.75 | 0.91 | 0.50 | 0.97 |
| AIBL study[45] | 0.85 | 0.85 | 0.41 | 0.98 |
| Peptoid approach[46] | 0.94 | 0.94 | 0.66 | 0.99 |
| Laske and colleagues[47] | 0.94 | 0.80 | 0.37 | 0.99 |

BR = base rate,
SN = sensitivity,
SP = specificity,
PPV = positive predictive value,
NPV = negative predictive value The findings from the present inventors' prior work as well as that from other research groups have also been included for comparison. As is clearly illustrated from above, the current novel procedure is the only procedure that can possibly be utilized in primary care settings in order to have an acceptable accuracy in referrals to specialty clinics. With the exception of the peptoid approach, no other efforts would be better than chance (i.e., 50%) when indicating to a primary care provider that a specialty referral would be needed.

TABLE 5

Diagnostic Accuracy of Blood-Based Screen for Neurodegenerative Diseases in Primary Care Settings

| | | | Base Rate = 11% | |
|---|---|---|---|---|
| | SN | P | PPV | NPV |
| Current Novel Procedure | 1.0 | 1.0 | 1.0 | 1.0 |
| 1998 Consensus Report minimal guidelines37 | 0.80 | 0.80 | 0.33 | 0.97 |

BR = base rate,
SN = sensitivity,
SP = specificity,
PPV = positive predictive value,
NPV = negative predictive value The current approach is 100% at identifying neurodegenerative diseases via the use of overall profiles. Given the very low prevalence of these diseases in the general population, the high accuracy is needed for appropriate referrals to specialist to be made by the primary care practitioners.

Combining specific biomarkers with select cognitive testing. In our recent work, we demonstrated that molecular profiles could be generated for neuropsychological test performance, and that these profiles accounted for upwards of 50% of the variance in test scores[48]. It was further demonstrated that specific serum-based biomarkers and select cognitive testing can be combined to refine the assessment process and increase diagnostic accuracy. In one example, only the top 2 markers were selected from the serum-algorithm (TNFα and IL7), in conjunction with a single, easy-to-administer cognitive test (in this example a 4-point clock drawing test, but other short and easy tests can be used, e.g., verbal fluency, trail making, list learning, and the like). When these 3 items were combined into a single logistic regression, 92% accuracy was found (SN=0.94, SP=0.90) in distinguishing all AD (n=150) from NC (n=150). When the sample was restricted only to mild AD (CDR global score<=1.0), an overall accuracy of 94% (SN=0.94, SP=0.83) was found. Lastly, and importantly, the sample was restricted only to very early AD (CDR global score=0.5), which resulted in an overall accuracy of 91% (SN=0.97, SP=0.72). These findings clearly demonstrate the possibility of combining specific biomarkers with select cognitive testing to refine the overall algorithm.

In summary, the current approach: (1) is highly accurate at detecting Alzheimer's disease; (2) is highly accurate at detecting and discriminating between neurodegenerative diseases; (3) can be implemented within primary care settings as the first step in a multi-stage diagnostic process; and (4) the combination of specific serum biomarkers and select neurocognitive screening assessments can refine the screening process with excellent accuracy.

FIG. 7 shows the selection of the specialist for referral, and hence the course of treatment, based on the results of the screen of the two or more biomarkers measured at the primary care center or point of care.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refer to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 8,9, 10, 11, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Villemagne V L, Rowe C C. Long night's journey into the day: Amyloid-β imaging in Alzheimer's disease. Journal of Alzheimer's Disease. 2013; 33(SUPPL. 1): S349-S359.
2. Pyykkö O T, Helisalmi S, Koivisto A M, et al. APOE4 predicts amyloid-β in cortical brain biopsy but not idiopathic normal pressure hydrocephalus. Journal of Neurology, Neurosurgery and Psychiatry. 2012; 83(11):1119-1124.
3. Benadiba M, Luurtsema G, Wichert-Ana L, Buchpigel C A, Filho G B. New molecular targets for PET and SPECT imaging in neurodegenerative diseases. Revista Brasileira de Psiquiatria 2012; 34(SUPPL2): S125-S148.
4. McKeith I G, Fairbairn A F, Bothwell R A, et al. An evaluation of the predictive validity and inter-rater reliability of clinical diagnostic criteria for senile dementia of Lewy body type. Neurology. 1994; 44(5):872-877.

5. Van Den Dungen P, Van Marwijk H W M, Van Der Horst H E, et al. The accuracy of family physicians' dementia diagnoses at different stages of dementia: A systematic review. International Journal of Geriatric Psychiatry. 2012; 27(4):342-354.
6. Löppönen M, Räihä I, Isoaho R, Vahlberg T, Kivelä S-L. Diagnosing cognitive impairment and dementia in primary health care—a more active approach is needed. Age and Ageing. Nov. 1, 2003 2003; 32(6):606-612.
7. Belmin J, Min L, Roth C, Reuben D, Wenger N. Assessment and management of patients with cognitive impairment and dementia in primary care. Journal of Nutrition, Health and Aging. 2012; 16(5):462-467.
8. Maeck L, Haak S, Knoblauch A, Stoppe G. Dementia diagnostics in primary care: a representative 8-year follow-up study in lower saxony, Germany. Dementia & Geriatric Cognitive Disorders. 2008; 25(2):127-134.
9. Fiss T, Thyrian J R, Fendrich K, Van Den Berg N, Hoffmann W. Cognitive impairment in primary ambulatory health care: Pharmacotherapy and the use of potentially inappropriate medicine. International Journal of Geriatric Psychiatry. 2013; 28(2):173-181.
10. Lo A, Ryder K, Shorr R I. Relationship between patient age and duration of physician visit in ambulatory setting: Does one size fit all? Journal of the American Geriatrics Society. 2005; 53(7):1162-1167.
11. Bond J, Graham N, Padovani A, MacKell J, Knox S, Atkinson J. Screening for cognitive impairment, Alzheimer's disease and other dementias: Opinions of European caregivers, payors, physicians and the general public. Journal of Nutrition, Health and Aging. 2010; 14(7):558-562.
12. Schneider P, Hampel H, Buerger K. Biological marker candidates of alzheimer's disease in blood, plasma, and serum. CNS Neuroscience and Therapeutics. 2009; 15(4): 358-374.
13. Alzheimer's Association. 2013 Alzheimer's Disease Facts and Figures. Alzheimer's & Dementia. 2013; 9(2): 1-72.
14. Shaw L M, Korecka M, Clark C M, Lee V M, Trojanowski J Q. Biomarkers of neurodegeneration for diagnosis and monitoring therapeutics. Nature Reviews. Drug Discovery. 2007; 6(4):295-303.
15. Thal L J, Kantarci K, Reiman E M, et al. The role of biomarkers in clinical trials for Alzheimer disease. Alzheimer Disease & Associated Disorders. 2006; 20(1): 6-15.
16. Martin M A, Swider S M, Olinger T, et al. Recruitment of Mexican American adults for an intensive diabetes intervention trial. Ethnicity and Disease. 2011; 21(1):7-12.
17. O'Bryant S E, Xiao G, Barber R, et al. A serum protein-based algorithm for the detection of Alzheimer disease. Archives of Neurology. 2010; 67(9):1077-1081.
18. O'Bryant S, Xiao, G, Barber, R, Reisch, J, Hall, J, Cullum, C M, Doody, R, Fairchild, T, Adams, P, Wilhelmsen, K, & Diaz-Arrastia, R. A blood based algorithm for the detection of Alzheimer's disease. Dementia and Geriatric Cognitive Disorders. 2011; 32:55-62.
19. O'Bryant S E, Xiao G, Barber R, et al. A Blood-Based Screening Tool for Alzheimer's Disease That Spans Serum and Plasma: Findings from TARC and ADNI. PLoS ONE. 2011; 6(12): e28092.
20. O'Bryant S E, Xiao G, Edwards M, et al. Biomarkers of Alzheimer's disease among Mexican Americans. Journal of Alzheimer's Disease. 2013; 34(4):841-849.
21. Waring S, O'Bryant, S E, Reisch, J S, Diaz-Arrastia, R, Knebl, J, Doody, R, for the Texas Alzheimer's Research Consortium. The Texas Alzheimer's Research Consortium longitudinal research cohort: Study design and baseline characteristics. Texas Public Health Journal. 2008; 60(3):9-13.
22. O'Bryant S E, Hobson V, Hall J R, et al. Brain-derived neurotrophic factor levels in alzheimer's disease. Journal of Alzheimer's Disease. 2009; 17(2):337-341.
23. McKhann D, Drockman, D., Folstein, M. et al. Clinical diagnosis of Alzheimer's disease: Report of the NINCDS-ADRDA Work Group. Neurology. 1984; 34:939-944.
24. Bjerke M, Portelius E, Minthon L, et al. Confounding factors influencing amyloid beta concentration in cerebrospinal fluid. International Journal of Alzheimer's Disease. 2010.
25. Kounnas M Z, Danks A M, Cheng S, et al. Modulation of γ-Secretase Reduces β-Amyloid Deposition in a Transgenic Mouse Model of Alzheimer's Disease. Neuron. 2010; 67(5):769-780.
26. Kuhle J, Regeniter A, Leppert D, et al. A highly sensitive electrochemiluminescence immunoassay for the neurofilament heavy chain protein. Journal of Neuroimmunology. 2010; 220(1-2):114-119.
27. Oh E S, Mielke M M, Rosenberg P B, et al. Comparison of conventional ELISA with electrochemiluminescence technology for detection of amyloid-β in plasma. Journal of Alzheimer's Disease. 2010; 21(3):769-773.
28. Alves G, Brønnick K, Aarsland D, et al. CSF amyloid-β and tau proteins, and cognitive performance, in early and untreated Parkinson's Disease: The Norwegian ParkWest study. Journal of Neurology, Neurosurgery and Psychiatry. 2010; 81(10):1080-1086.
29. O'Bryant S E, Xiao G, Barber R, et al. A blood-based algorithm for the detection of Alzheimer's disease. Dementia and Geriatric Cognitive Disorders. 2011; 32(1): 55-62.
30. R_Development_Core_Team. R: A language and environment for statistical computing. 2009; www.R-project.org.
31. Breiman L. Random forests. Machine Learning. 2001; 45(1):5-32.
32. O'Bryant S E X G, Edwards M, Devous M D, Gupta V, Martins R, Zhang F, Barber R C for the Texas Alzheimer's Research Consortium. Biomarkers of Alzheimer's Disease Among Mexican Americans. Journal of Alzheimer's Disease. 2013, in press.
33. Dickstein D L, Walsh J, Brautigam H, Stockton Jr S D, Gandy S, Hof P R. Role of vascular risk factors and vascular dysfunction in Alzheimer's disease. Mount Sinai Journal of Medicine. 2010; 77(1):82-102.
34. Piazza F, Galimberti G, Conti E, et al. Increased tissue factor pathway inhibitor and homocysteine in Alzheimer's disease. Neurobiology of Aging. 2010.
35. Okereke O I, Selkoe D J, Pollak M N, et al. A profile of impaired insulin degradation in relation to late-life cognitive decline: A preliminary investigation. International Journal of Geriatric Psychiatry. 2009; 24(2):177-182.
36. van Oijen M, Hofman A, Soares H D, Koudstaal P J, Breteler M M. Plasma Abeta(1-40) and Abeta(1-42) and the risk of dementia: a prospective case-cohort study. [see comment]. Lancet Neurology. 2006; 5(8): 655-660.
37. Anonymous. Consensus report of the Working Group on: "Molecular and Biochemical Markers of Alzheimer's Disease". The Ronald and Nancy Reagan Research Institute of the Alzheimer's Association and the National Institute on Aging Working Group. [see comment][erratum appears in Neurobiol Aging 1998 May-June; 19(3): 285]. Neurobiology of Aging. 1998; 19(2):109-116.
38. O'Bryant S E, Lucas J A. Estimating the predictive value of the Test of Memory Malingering: An illustrative example for clinicians. Clinical Neuropsychologist. 2006; 20(3):533-540.
39. Bauer L, O'Bryant S E, Lynch J K, McCaffrey R J, Fisher J M. Examining the test of memory malingering trial 1 and word memory test immediate recognition as screening tools for insufficient effort. Assessment. 2007; 14(3):215-222.
40. Clark J H, Hobson V L, O'Bryant S E. Diagnostic accuracy of % retention scores on RBANS verbal memory subtests for the diagnosis of Alzheimer's disease and mild cognitive impairment. Archives of Clinical Neuropsychology. 2010; 25(4):318-326.
41. Duff K, Humphreys Clark J D, O'Bryant S E, Mold J W, Schiffer R B, Sutker P B. Utility of the RBANS in detecting cognitive impairment associated with Alzheimer's disease: Sensitivity, specificity, and positive and negative predictive powers. Archives of Clinical Neuropsychology. 2008; 23(5):603-612.
42. Duff K, Hobson V L, Beglinger L J, O'Bryant S E. Diagnostic accuracy of the RBANS in mild cognitive impairment: Limitations on assessing milder impairments. Archives of Clinical Neuropsychology. 2010; 25(5): 429-441.
43. O'Bryant S E, Humphreys J D, Smith G E, et al. Detecting dementia with the mini-mental state examination in highly educated individuals. Archives of Neurology. 2008; 65(7):963-967.
44. O'Bryant S E, Lucas J A, Willis F B, Smith G E, Graff-Radford N R, Ivnik R J. Discrepancies between self-reported years of education and estimated reading level among elderly community-dwelling African-Americans: Analysis of the MOAANS data. Archives of Clinical Neuropsychology. 2007; 22(3):327-332.
45. Doecke J, Laws, S M, Faux, N G, Wilson, W, Burnham, S C, Lam, C P, Mondal, A, Bedo, J, Busy, A I, Brown, B, De Ruyck, K, Ellis, K A, Fowler, C, Gupta, V B, Head, R, Macaulay, L, Fertile, K, Rowe, C C, Rembach, A, Rodrigues, M, Rumble, R, Szoeke, C, Taddei, K, Taddei, T, Trounson, B, Aimes, D, Masters, C L, Martins, R N. Blood-based protein biomarkers for the diagnosis of Alzheimer's disease. Arch Neurol. 2012; published online.
46. Reddy M M, Wilson R, Wilson J, et al. Identification of candidate IgG biomarkers for alzheimer's disease via combinatorial library screening. Cell. 2011; 144(1):132-142.
47. Laske C L T, Stransky E, Hoffmann N, Fallgatter A J, Dietzsch J. Identification of a blood-based biomarker panel for classification of Alzheimer's disease. International Journal of Neuropsychopharmacology. 2011; 14(9): 1147-1155.
48. O'Bryant S E G X, Barber R C, Cullum C M, Weiner M, Hall J, Edwards M, Grammas P, Wilhelmsen K, Doody R, Diaz-Arrastia R. Molecular neuropsychology: creation of test-specific blood biomarker algorithms. Dementia and Geriatric Cognitive Disorders. 2013, in press.

The invention claimed is:

1. A method of screening biomarkers in a primary care setting, the method consisting of:
obtaining a blood sample from a subject suffering from cognitive impairment, and
measuring expression levels of each biomarker in the group consisting of:
interleukin-7 (IL7),
tumor necrosis factor alpha (TNFα),
interleukin-5 (IL5), and
interleukin-6 (IL6),
wherein the measuring is done with a nucleic acid assay, an immunoassay, chemiluminescence detection, electrochemiluminescence detection, or an enzymatic activity assay.

2. The method of claim 1, wherein the subject is determined to suffer from cognitive impairment for having a lower score in at least one neurocognitive evaluation selected from the group consisting of a clock drawing test, verbal fluency test, trail making test, list learning test, sleep disturbances, visual hallucinations, behavioral disturbances, motor disturbances, and any combinations thereof, as compared to a normal subject.

3. The method of claim 1, wherein the blood sample is a serum or a plasma sample.

4. A method of screening biomarkers in a primary care setting, the method consisting of:
obtaining a blood sample from a subject suffering from cognitive impairment, and
measuring expression levels of each biomarker in the group consisting of:
interleukin-7 (IL7),
tumor necrosis factor alpha (TNFα),
interleukin-5 (IL5),
interleukin-6 (IL6), and
C-reactive protein (CRP),
wherein the measuring is done with a nucleic acid assay, an immunoassay, chemiluminescence detection, electrochemiluminescence detection, or an enzymatic activity assay.

5. A method of screening biomarkers in a primary care setting, the method consisting of:
obtaining a blood sample from a subject suffering from cognitive impairment, and
measuring expression levels of each biomarker in the group consisting of:
IL-7, and
TNFα,
wherein the measuring is done with a nucleic acid assay, an immunoassay, chemiluminescence detection, electrochemiluminescence detection, or an enzymatic activity assay.

6. The method of claim 5, wherein the subject is determined to suffer from cognitive impairment for having a lower score in at least one neurocognitive evaluation selected from the group consisting of clock drawing test, verbal fluency test, trail making test, list learning test, sleep disturbances, visual hallucinations, behavioral disturbances, motor disturbances, and any combinations thereof, as compared to a normal subject.

* * * * *